United States Patent
Zhu et al.

(10) Patent No.: US 10,654,851 B2
(45) Date of Patent: May 19, 2020

(54) DEUTERATED 3-(4,5-SUBSTITUTED AMINOPYRIMIDINE)PHENYL DERIVATIVES AND USE THEREOF

(71) Applicant: NANJING CHUANGTE PHARMACEUTICAL TECHNOLOGY CO., LTD, Nanjing (CN)

(72) Inventors: Yongqiang Zhu, Nanjing (CN); Zhaogang Liu, Nanjing (CN); Chao Feng, Nanjing (CN); Shihe Hu, Nanjing (CN); Hao Chen, Nanjing (CN); Enhe Bai, Nanjing (CN); Jie Wang, Nanjing (CN); Jingmiao Shi, Nanjing (CN)

(73) Assignee: NANJING CHUANGTE PHARMACEUTICAL TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 16/333,700

(22) PCT Filed: Sep. 18, 2017

(86) PCT No.: PCT/CN2017/102027
§ 371 (c)(1),
(2) Date: Mar. 15, 2019

(87) PCT Pub. No.: WO2018/050108
PCT Pub. Date: Mar. 22, 2018

(65) Prior Publication Data
US 2019/0225610 A1    Jul. 25, 2019

(30) Foreign Application Priority Data
Sep. 19, 2016 (CN) ............ 2016 1 0833361
Jun. 5, 2017 (CN) ............ 2017 1 0413610

(51) Int. Cl.
| C07D 471/06 | (2006.01) |
|---|---|
| A61P 35/00 | (2006.01) |
| A61P 35/02 | (2006.01) |
| A61K 31/506 | (2006.01) |
| C07B 59/00 | (2006.01) |

(52) U.S. Cl.
CPC .......... C07D 471/06 (2013.01); A61K 31/506 (2013.01); A61P 35/00 (2018.01); A61P 35/02 (2018.01); C07B 59/002 (2013.01); C07B 2200/05 (2013.01)

(58) Field of Classification Search
CPC ........ C07D 471/06; A61P 35/02; A61P 35/00; A61K 31/506; C07B 59/002
USPC ....................................... 544/331
See application file for complete search history.

(56) References Cited

U.S. PATENT DOCUMENTS

2017/0313714 A1* 11/2017 Wei ............... C07D 403/12
2018/0016258 A1*  1/2018 Zhu .................. A61K 31/506

FOREIGN PATENT DOCUMENTS

| CN | 104140418 | * | 11/2014 | .......... C07D 403/04 |
| CN | 107344934 | * | 11/2017 | .......... C07D 471/06 |
| WO | WO-2015175632 A1 | * | 11/2015 | .......... C07D 471/06 |
| WO | WO-2016029839 A1 | * | 3/2016 | .......... A61K 31/506 |
| WO | WO-2019174623 A1 | * | 9/2019 | ............ C07B 59/00 |

OTHER PUBLICATIONS

Janne; N Engl J Med 2015, 372, 1689-1699. DOI: 10.1056/NEJMoa1411817 (Year: 2015).*
Wieduwilt; Cell. Mol. Life Sci. 2008, 65, 1566-1584. DOI: 10.1007/s00018-008-7440-8 (Year: 2008).*
Zhang; European Journal of Medicinal Chemistry 2017, 135, 12-23, with supporting information, 53 pages. Doi: 10.1016/j.ejmech.2017.04.036 (Year: 2017).*
Huynh; Inflammation & Cell Signaling 2015, 2, e840, 4 pages. doi: 10.14800/ics.840 (Year: 2015).*
Gant; J. Med. Chem. 2014, 57, 9, 3595-3611. DOI: 10.1021/jm04007998 (Year: 2014).*

* cited by examiner

*Primary Examiner* — Daniel R Carcanague
(74) *Attorney, Agent, or Firm* — CBM Patent Consulting, LLC

(57) ABSTRACT

A type of deuterated 3-(4,5-substituted aminopyrimidine) phenyl derivatives and use thereof. The derivatives are compounds of Formula (I) or pharmaceutically acceptable salts thereof. These compounds or salts thereof can be used for treatment or prevention of diseases or illnesses through certain mutant forms of epidermal growth factor receptors, inhibit the growth of various tumor cells effectively, and inhibit other proteases of EGFR and Her families, they can be used for preparing anti-tumor drugs.

7 Claims, No Drawings

DEUTERATED 3-(4,5-SUBSTITUTED AMINOPYRIMIDINE)PHENYL DERIVATIVES AND USE THEREOF

TECHNICAL FIELD

The present invention relates to the field of anti-tumor drugs, and specifically relates to deuterated 3-(4,5-substituted aminopyrimidine)phenyl derivatives and use in preparation of anti-tumor drugs.

BACKGROUND ART

Chemotherapy is the main treatment means in traditional cancer treatment. Chemotherapy drugs block cell division non-specifically to cause cell death, and they also destroy the growth of normal human cells greatly while killing tumor cells to bring many adverse reactions. Many people are pessimistic and even give up the treatment because they concern about the serious side effects of chemotherapy. In addition, the chemotherapy for non-small cell lung cancer (NSCLC) is not optimistic due to the drug resistance of chemotherapy drugs, and the extension of the chemotherapy cycle only increases the toxic or side effect, but not the efficacy. At the same time, NSCLC cells are not sensitive to chemotherapy or conventional chemotherapy, and the overall response rate is only about 25%. The five-year survival rate of NSCLC patients is less than 20% due to these reasons.

Among 50%-80% of NSCLC patients, their epidermal growth factor receptors (EGFRs) are over-expressed, causing canceration. There are two main types of EGFR-targeted drugs: one is a small molecule tyrosine kinase inhibitor (TKI) that acts on the intracellular region of the receptor; and the other one is a monoclonal antibody (MAb) that acts on the extracellular region of the receptor. The first-generation EGFR inhibitors that have been used in clinic, such as iressa, erlotinib and lapatinib, have achieved a great success in the treatment of NSCLC, and have improved the five-year survival rate of NSCLC patients. At the same time, compared with the chemotherapy, they have the advantage of not causing side effects such as myelosuppression, nausea and neurotoxicity; however, they are less effective when they are used for treating alone and have obvious side effects such as rash and diarrhea, and the patients have resistance to the drugs after one-year treatment. Research suggested that the mutation at the T790M locus of the EGFR gene is the main cause of drug resistance to such drugs. Clinical case data show that patients' acquired drug resistance of approximately 50% is derived from the mutation at the T790M locus. Further studies confirmed that the mutation at the T790M of the EGFR gene, i.e., the conversion of encoded threonine into methionine, caused the steric hindrance to hinder the binding of the inhibitor to the ATP binding region and ultimately resulted in the loss of activity of the inhibitors. Studies have also shown at present that the mutation at the T790M locus did not directly affect the affinity of the inhibitor to the EGFR, but greatly increased the affinity of the EGFR to ATP, resulting in a relatively significant decrease in the affinity of the inhibitor to the EGFR (the inhibitor was competitively bound with the ATP). The second-generation inhibitors such as afatinib and dacomitinib, superior to the first generation, were characterized by the increase of recognition on EGFR, and can distinguish tumor cells from normal cells, thus reducing the side effects. However, the poor selectivity of these molecules for T790M mutants of EGFR results in lower clinically tolerated doses of drugs. Under the maximum tolerated dose (MTD), the drugs cannot reach an effective concentration in vivo and are ineffective for most drug-resistant patients.

In short, the conventional EGFR-TKI still cannot solve the clinical needs caused by drug resistance, and the conventional drugs are mostly reversible or irreversible EGFR inhibitors with quinazoline or quinolinamine as the basic nucleus, which have poor selectivity on wild-type cells to cause inevitable toxic or side effects. Therefore, new types, especially novel skeletons of compounds are urgently needed in clinic to solve the problems of drug resistance, poor selectivity and the like.

SUMMARY OF THE INVENTION

A purpose of the present invention is to provide a type of deuterated 3-(4,5-substituted aminopyrimidine)phenyl derivatives.

The purpose of the present invention can be achieved by the following measures:

The deuterated 3-(4,5-substituted aminopyrimidine)phenyl derivatives of the present invention are compounds of Formula (I) or pharmaceutically acceptable salts thereof,

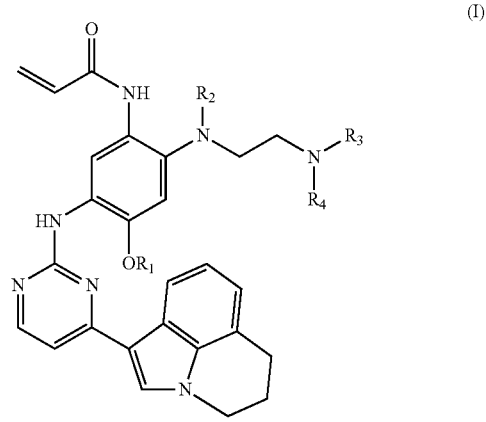

(I)

wherein $R_1$ and $R_2$ are selected from the group consisting of —$CH_3$ or —$CD_3$, $R_3$ and $R_4$ are selected from the group consisting of —$CH_3$, $CD_3$ or H, and at least one of $R_1$, $R_2$, $R_3$ and $R_4$ is —$CD_3$.

Further, in the compounds of Formula (I), preferably $R_1$ is —$CH_3$.

Compounds or pharmaceutically acceptable salts thereof, some specific compounds are selected from:

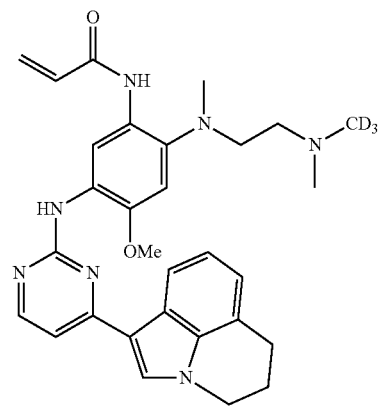

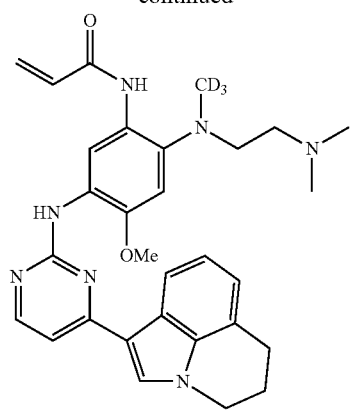
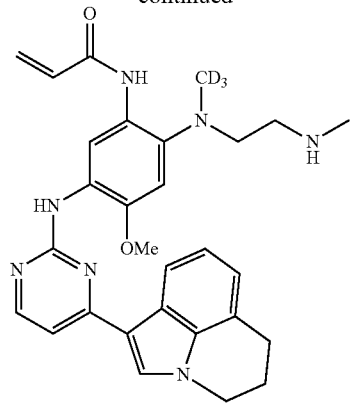
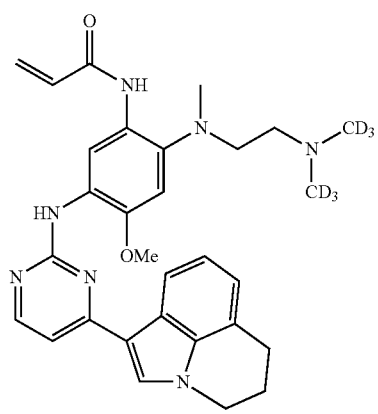
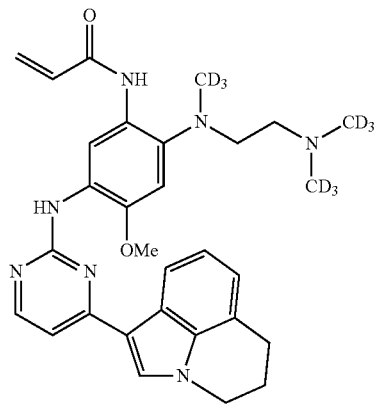
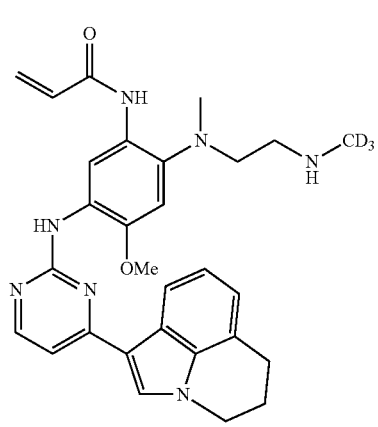
The preparation route of the compounds of Formula (I) is as follows:
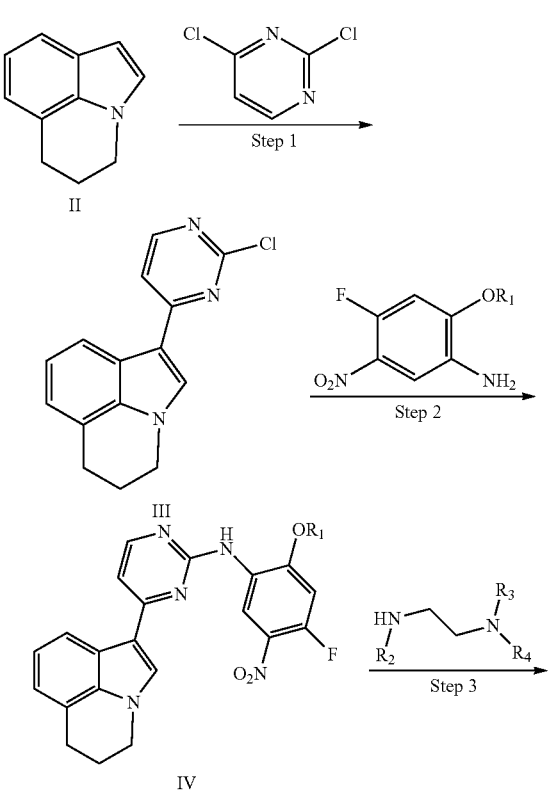

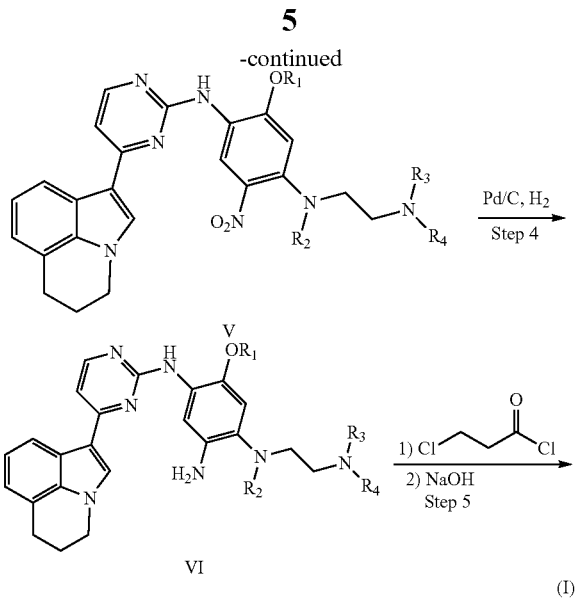

The specific steps of the preparation route are as follows:

step 1: dissolving the compound II and 2,4-dichloropyrimidine into a solvent, and obtaining III by nucleophilic substitution reaction in the presence of a Lewis acid, wherein the solvent is selected from 1,2-dimethoxyethane (DME), toluene, chlorobenzene or a mixture thereof, and the Lewis acid is selected from aluminum trichloride or boron trifluoride;

step 2: dissolving the intermediate III and 4-fluoro-2-methoxy-5-nitroaniline into a solvent, and obtaining IV under the action of p-toluenesulfonic acid, wherein the solvent is selected from 1,4-dioxane, N,N-dimethylformamide (DMF) or a mixture thereof;

step 3: dissolving the intermediate IV and an organic amine into a solvent, and reacting under the action of DIPEA to obtain an intermediate V, wherein the solvent is selected from dimethyl adipate (DMA), dimethyl acetamide (DMAc), N,N-dimethylformamide (DMF) or a mixture thereof;

step 4: dissolving the intermediate V into a solvent, and reducing the intermediate V to an intermediate VI using Pd/C as a reducing agent, wherein the solvent is selected from methanol or ethanol;

step 5: reacting the intermediate VI with chloropropionyl chloride by using tetrahydrofuran/water as a solvent to obtain an intermediate compound, and directly adding sodium hydroxide without separation for continuous reaction to obtain the compounds having the structure of Formula (I).

Salts which may be formed by the compounds in the present invention also fall within the scope of the present invention. Unless otherwise stated, the compounds in the present invention are understood to include the salts thereof. For example, the compounds of Formula (I) are reacted with an amount of, e.g., an equivalent amount of acid or alkali, salts are separated out in a medium, or salts are obtained by freeze-drying in an aqueous solution. The alkali fragments contained in the compounds of the present invention, including but not limited to amines or pyridine or imidazole rings, may form salts with organic or inorganic acids. The typical salts that may be formed include acetate, adipate, alginate, ascorbate, aspartate, benzoate, besylate, p-toluenesulfonate, hydrosulfate, borate, butyrate, citrate, camphor salt, camphor sulfonate, cyclopentane propionate, diglycolate, lauryl sulfate, ethane sulfonate, fumarate, gluceptate, glycerol phosphate, enanthate, hexanoate, hydrochloride, hydrobromide, hydroiodide, hydroxyethanesulfonate, lactate, maleate, methanesulfonate, naphthalene sulfonate, nicotinate, nitrate, oxalate, pectate, persulfate, phenpropionate, phosphate, picrate, pivalate, propionate, salicylate, succinate, sulfate, sulfonate, tartrate, and thiocyanate.

Among the compounds of the present invention, the compounds obtained by successive preparation, separation and purification are more than or equal to 90%, for example, more than or equal to 95%, more than or equal to 99% ("very pure" compounds), by weight, which will be described in the detailed description. "Very pure" compounds of the present invention are also part of the present invention.

The present invention further provides use of the compounds or a pharmaceutically acceptable salt of Formula (I) or pharmaceutically acceptable salts thereof in the manufacture of a medicament for the treatment or prevention of tumors.

The tumors include, but are not limited to, non-small cell lung cancer, small cell lung cancer, pancreatic cancer, breast cancer, prostate cancer, liver cancer, skin cancer, epithelial cell cancer, gastrointestinal stromal tumor, leukemia, histiocytic lymphoma, and nasopharyngeal cancer.

One aspect of the present invention provides compounds of Formula (I) for use in treatment or prevention of diseases, dysfunction, disorders or illnesses associated with EGFRs or associated with EGFRs in the form of activating mutants or resistant mutants.

The diseases, dysfunction, disorders or illnesses associated with EGFRs or associated with EGFRs in the form of activating mutants or resistant mutants include, but are not limited to, non-small cell lung cancer, small cell lung cancer, pancreatic cancer, breast cancer, prostate cancer, liver cancer, skin cancer, epithelial cell cancer, gastrointestinal stromal tumor, leukemia, histiocytic lymphoma or nasopharyngeal cancer.

The EGFRs in the form of activating mutants or resistant mutants include, but are not limited to, L858R activating mutants, Exon19 deletion activating mutants and T790M resistant mutants.

The compounds of Formula (I) of the present invention may be combined with known therapy or other drugs for improving similar diseases. In the case of combined administration, the administration method and dosage of the conventional drugs remain unchanged, while the compound of Formula (I) is administered simultaneously or subsequently. When the compound of Formula (I) is administered simultaneously with one or more other drugs, a pharmaceutical composition containing both one or more known drugs and the compound of Formula (I) is preferred. The combined administration of drugs also includes administration of a compound of Formula (I) with one or more other known drugs over an overlapping period of time. When the compound of Formula (I) is administered with one or more other drugs, the dose of the compound of Formula (I) or the known drugs may be lower than when they are administered alone. The drugs or active ingredients which may be administered with the compounds of Formula (I) include, but are not limited to, the followings:

estrogen receptor regulators, androgen receptor regulators, retinal receptor regulators, cytotoxins/cytostatics, antiproliferative agents, protein transferase inhibitors, HMG-CoA reductase inhibitors, HIV protein kinase inhibitors, reverse transcriptase inhibitors, angiogenesis inhibitors, cell proliferation and survival signal inhibitors, drugs that interfere with cell cycle checkpoints, apoptosis inducers, cytotoxic drugs, tyrosine protein inhibitors, EGFR inhibitors, VEGFR inhibitors, serine/threonine protein inhibitors, Bcr-Abl inhibitors, c-Kit inhibitors, Met inhibitors, Raf inhibitors, MEK inhibitors, MMP inhibitors, topoisomerase inhibitors, histone deacetylase inhibitors, proteosome inhibitors, CDK inhibitors, Bcl-2 family protein inhibitors, MDM2 family protein inhibitors, IAP family protein inhibitors, STAT family protein inhibitors, PI3K inhibitors, ATK inhibitors, integrin blockers, interferons, interleukin-12, COX-2 inhibitors, P53, P53 activators, VEGF antibodies, EGF antibodies, etc.

In one embodiment, the drugs or active ingredients that can be administered with the compounds of Formula (I) include, but are not limited to, the followings: aldesleukin, alendronic acid, interferon, alitretinoin, allopurinol, allopurinol sodium, palonosetron hydrochloride, altretamine, aminoglutethimide, amifostine, amrubicin, amsacrine, anastrozole, dolasetron, aranesp, arglabin, arsenic trioxide, aromasin, 5-azacytidine, azathioprine, BCG vaccine or tice BCG vaccine, bestatin, betamethasone acetate, betamethasone sodium phosphate inhibitor, bexarotene, bleomycin sulfate, bromouridine, bortezomib, kyprolis, busulfan, calcitonin, alemtuzumab monoclonal antibody injection, capecitabine, carboplatin, casodex, cefesone, celmoleukin, daunorubicin, chlorambucil, cisplatin, cladribine, clodronic acid, cyclophosphamide, cytarabine, dacarbazine, actinomycin D, daunorubicin liposome, dexamethasone, dexamethasone phosphate, estradiol valerate, denileukin diftitox 2, depo-medrol, deslorelin, dexrazoxane, diethylstilbestrol, diflucan, docetaxel, doxifluridine, doxorubicin, dronabinol, holmium-166-chitosan complex, eligrand, rasburicase, epirubicin hydrochloride, aprepitant, epirubicin, epoetin alfa, erythropoietin, eptaplatin, levamisole tablets, estradiol inhibitors, 17-β-estradiol, estramustine sodium phosphate, ethinylestradiol, amifostine, hydroxyphosphoric acid, etopophos, etoposide, fadrozole, tamoxifen preparation, filgrastim, finasteride, floxuridine, fluconazole, fludarabine, 5-fluorodeoxyuridine monophosphate, 5-fluorouracil, fluoxymesterone, flutamide, formestane, 1-pyrimidine, arabinofuranose cytidine-5 furan stearoyl phosphate, fotemustine, fulvestrant, gamma globulin, gemcitabine, gemtuzumab ozogamicin, imatinib mesylate, carmustine rice paper capsules, goserelin, granisetron hydrochloride, histrelin, topotecan hydrochloride, hydrocortisone, erythro-hydroxynonyl adenine, hydroxyurea, ibritumomab tiuxetan, idarubicin, ifosfamide, interleukin-2, intron A, iressa, irinotecan, kytril, lentinan sulfate, letrozole, leucovorin, leuprolide, leuprolide acetate, levamisole, calcium levofolinate, levothyroxine sodium, levothyroxine sodium preparation, lomustine, lonidamine, dronabinol, nitrogen mustard, mecobalamin, medroxyprogesterone acetate, megestrol acetate, melphalan, esterified estrogen, 6-mercaptopurine, mesna, methotrexate, methyl aminolevulinate, miltefosine, minocycline, mitomycin C, mitotane, mitoxantrone, trilostane, doxorubicin citrate liposome, nedaplatin, pegylated filgrastim, oprelvekin, neupogen, nilutamide, tamoxifen, NSC-631570, recombinant human interleukin-1 group, octreotide, ondansetron hydrochloride, dehydrocortisone oral solution, oxaliplatin, paclitaxel, prednisone sodium phosphate preparation, pegaspargase, pegasys, pentostatin, picibanil, pilocarpine hydrochloride, pirarubicin, plicamycin, porfimer sodium, prednimustine, prednisolone steaglate, prednisone, premarin, procarbazine, recombinant human erythropoietin, raltitrexed, rebif, rhenium-186 etidronate, rituximab, redoxon-A, romurtide, pilocarpine hydrochloride tablets, octreotide, sargramostim, semustine, sizofiran, sobuzoxane, methylprednisolone sodium succinate, spar-fosic acid, stem cell therapy, streptozocin, strontium-89 chloride, levothyroxine sodium, tamoxifen, tamsulosin, tasonermin, tastolactone, taxotere, teceleukin, temozolomide, teniposide, testosterone propionate, thioguanine, thiotepa, thyroid stimulating hormone, tiludronic acid, topotecan, toremifene, tositumomab, trastuzumab, treosulfan, retinoic acid, methotrexate tablets, trimethyl melamine, trimetrexate, triptorelin acetate, triptorelin pamoate, UFT, uridine, valrubicin, vesnarinone, vinblastine, vincristine, vindesine, vinorelbine, virulizine, dexrazoxane, zinostatin stimalamer, ondansetron, paclitaxel protein stablizer, acolbifene, affinitak, aminopterin, arzoxifene, asoprisnil, atamestane, BAY43-9006, avastin, CCI-779, CDC-501, celebrex, cetuximab, crisnatol, cyproterone acetate, decitabine, DN-101/doxorubicin-MTC, dSLIM, dutasteride, edotecarin, eflornithine, exatecan, fenretinide, histamine dihydrochloride, histrelin hydrogel implant, holmium-166 DOTMP, ibandronic acid, ixabepilone, keyhole limpet hemocyanin, L-651582, lanreotide, lasofoxifene, libra, lonafamib, miproxifene, minodronate, MS-209, liposome MEP-PE, MX-6, nafarelin, nemorubicin, neovastat, nolatrexed, oblimersen, onco-TCS, osidem, paclitaxel polyglutamate, pamidronate, PN-401, OS-21, quazepam, R-1549, raloxifene, ranpirnase, 13-cis-retinoic acid, satraplatin, seocalcitol, T-138067, tarceva, paclitaxel docosahexaenoate, thymosin a, tiazofurine, tipifarnib, tirapazamine, TLK-286, toremifene, trans-MID-lo7R, valspodar, vapreotide, vatalanob, verteporfin, vinflunine, Z-100 and zoledronic acid or a combination thereof.

The present invention further provides a pharmaceutical composition comprising the compounds of Formula (I) or pharmaceutically acceptable salts thereof and pharmaceutically acceptable adjuvants or carriers. "Pharmaceutically acceptable adjuvants or carriers" refer to pharmaceutically acceptable materials, ingredients or media, such as liquid or solid fillers, diluents, adjuvants, solvents or encapsulating materials, including main pharmaceutical agents carried or transported from an organ or a part of the body to the other organ or a part of the body. Each carrier must be "acceptable" and compatible with other forms of pharmaceutical ingredients, and without harm to patients. Some examples of the pharmaceutically acceptable carriers include: sugars such as lactose, glucose and sucrose; starches such as wheat starch and potato starch; cellulose and derivatives thereof such as sodium carboxymethylcellulose, ethyl cellulose, cellulose acetate, powdered tragacanth, malt, gelatin, talcum powder; adjuvants such as cocoa butter and suppository wax; oils such as peanut oil, cottonseed oil, safflower oil, sesame oil, olive oil, corn oil and soybean oil; glycols such as butanediol; polyols such as glycerol, sorbitol, mannitol and polyethylene glycol; esters such as ethyl oleate and ethyl laurate; agar; buffers such as magnesium hydroxide and aluminum hydroxide; alginic acid; pyrogen-free water; physiological saline; Ringer's solution; ethanol; phosphate buffer, and other non-toxic compatible substances applied in pharmaceutical preparations.

When the compounds of the present invention are administered to humans and animals as pharmaceutical agents, they can be administered as drugs themselves or as pharmaceutical compositions. For example, the compounds include 0.1% to 99.5% (preferably 0.5% to 90%) of active ingredients, and pharmaceutically acceptable carriers.

The compounds of the present invention may be administered by intravenous injection, intramuscular injection, intraperitoneal injection, subcutaneous injection, external use, oral administration, or other acceptable means.

The present invention further provides a pharmaceutical package or kit comprising one or more packages, and containing a pharmaceutical composition consisting of one or more ingredients of the present invention. The optional packages are produced in the form of announcements by government agencies, and both pharmaceutical or biological products and therapeutic preparations for humans are used or sold by disclosed methods permitted in production regulations.

Compared with the prior art, the present invention has the following beneficial effects:

The deuterated compounds of the present invention have enzyme and cell level bioactivities similar to AZD9291 and lower cardiotoxicity. The deuterated compounds of the present invention provide more options for novel anti-tumor drugs, and have good prospects for drug use.

DETAILED DESCRIPTION OF THE INVENTION

The following representative examples help to describe the present invention, but are not intended to or should not be interpreted as limiting the scope of the present invention. In fact, besides those appearing and described herein, the entire contents of the documents in the present invention, including the examples of scientific literatures and patents cited herein, and various modifications and many further variations resulting therefrom, are generally clear for those skilled in the art. It should also be understood that the references cited help to illustrate the contents of the present invention.

Example 1

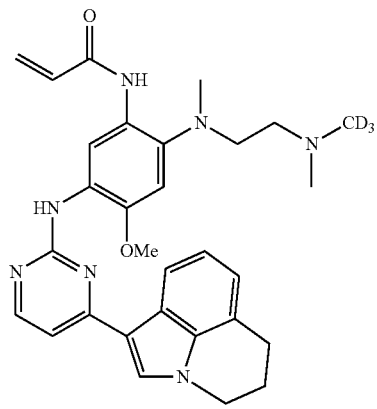 [SMILES: [2H]C([2H])([2H])N(C)CCN(C)c1cc(OC)c(Nc2nccc(-c3cn4c5c(cccc35)CCC4)n2)cc1NC(=O)C=C]

The synthetic route is as follows:

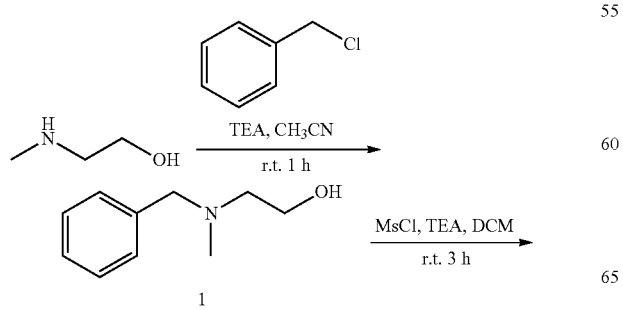

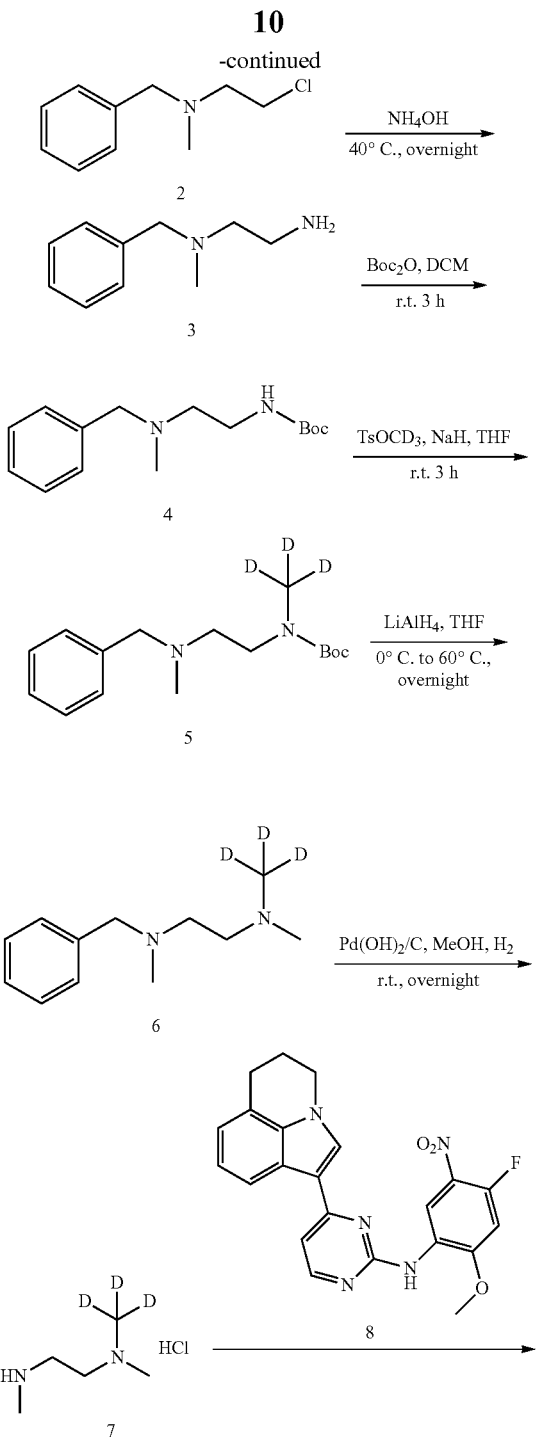

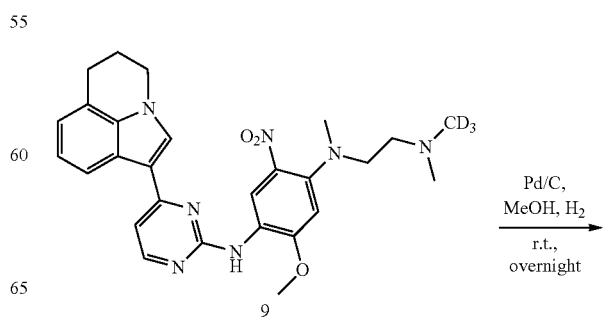

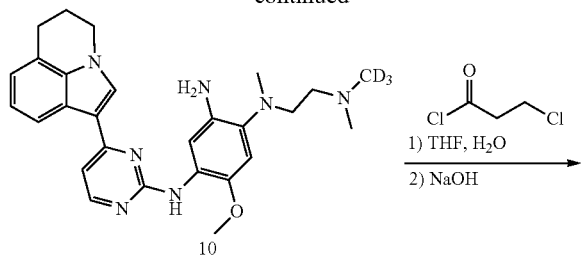

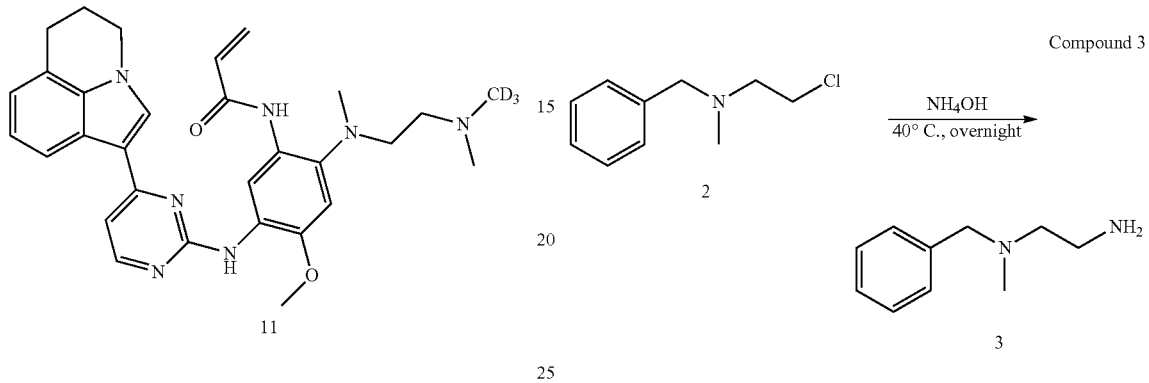

The compound 1 (21 g, 127.1 mmol), TEA (25.7 g, 254.2 mmol) and DCM (100 ml) were added into a 250 mL eggplant type bottle, and then MsCl (14.6 g, 127.1 mmol) was dripped at 0° C. The reaction solution was stirred at room temperature for 3 h, TLC was performed to ensure that no raw materials remained, the solvent was evaporated under reduced pressure, and the product was purified by column chromatography to obtain 20 g of light yellow liquid, i.e., compound 2, yield 85.6%.

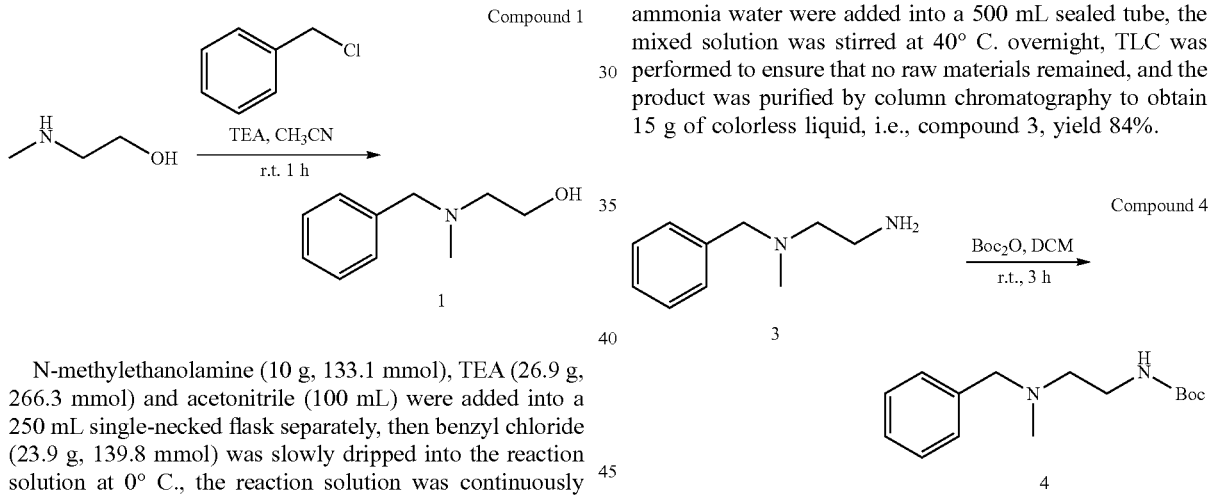

N-methylethanolamine (10 g, 133.1 mmol), TEA (26.9 g, 266.3 mmol) and acetonitrile (100 mL) were added into a 250 mL single-necked flask separately, then benzyl chloride (23.9 g, 139.8 mmol) was slowly dripped into the reaction solution at 0° C., the reaction solution was continuously stirred at room temperature for 1 h, TLC (Thin-Layer Chromatography) was performed to ensure that no raw materials remained, the solvent was evaporated under reduced pressure, and the product was purified by column chromatography to obtain 21 g of colorless liquid, i.e., compound 1, yield 95.5%.

The compound 2 (20 g, 108.9 mmol) and 215 mL of ammonia water were added into a 500 mL sealed tube, the mixed solution was stirred at 40° C. overnight, TLC was performed to ensure that no raw materials remained, and the product was purified by column chromatography to obtain 15 g of colorless liquid, i.e., compound 3, yield 84%.

The compound 3 (15 g, 91.3 mmol) and DCM (200 mL) were added into a 500 mL eggplant type bottle, Boc₂O (19.9 g, 91.3 mmol) was slowly dripped at room temperature, the mixed solution was continuously stirred at room temperature for 3 h after completion of dripping, TLC was performed to ensure that no raw materials remained, the solvent was evaporated under reduced pressure, and the product was purified by column chromatography to obtain 21 g of compound 4 that was a white solid, yield 87%.

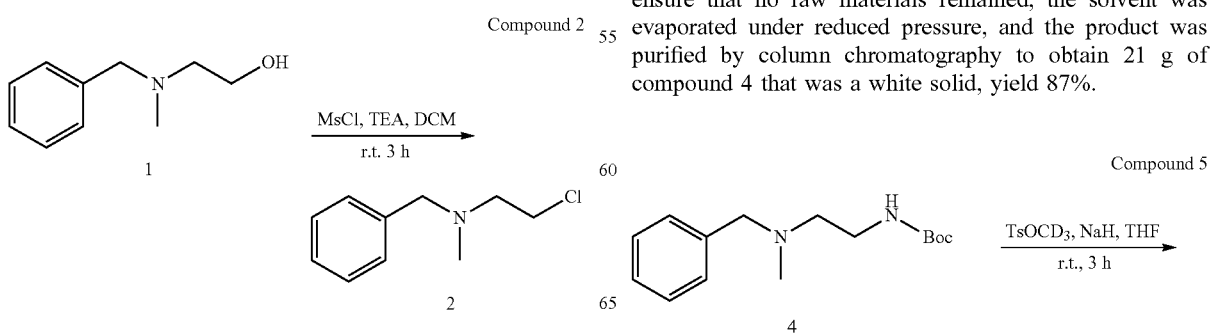

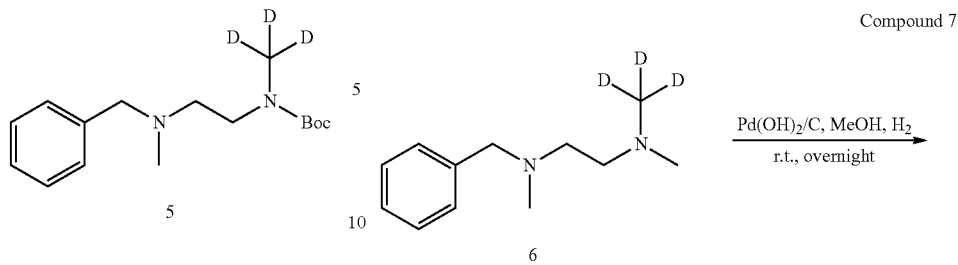

Compound 5

The compound 4 (10 g, 37.8 mmol) and DMF (40 mL) were added into a 100 mL eggplant type bottle, then NaH (2.3 g, 56.7 mmol) was added in portions, the solution was stirred for 30 mins, a DMF (10 mL) solution of TsOCD$_3$ (7.9 g, 41.6 mmol) was added, then the solution was stirred at room temperature for 3 h, TLC was perform to ensure that no raw materials remained, 150 mL of H$_2$O was added for quenching, extraction was performed with EA (50 mL*3), the organic phases were combined, washed with brine, and dried over anhydrous Na$_2$SO$_4$, the solvent was evaporated under reduced pressure, and the product was purified by column chromatography to obtain 8.5 g of compound 5 that was a white solid, yield 80%.

Compound 6

The compound 5 (8.5 g, 30.18 mmol) and THF (80 ml) were added into a 250 mL eggplant type bottle, LiAlH$_4$ (3.4 g, 90.59 mmol) was added in portions in an ice bath, then heating was performed to 60° C. overnight until no raw materials remained by TLC inspection, Na$_2$SO$_4$.10H$_2$O was added for quenching, the solid was removed by filtration, the filtrate was collected, the solvent was evaporated under reduced pressure, and the product was purified by column chromatography to obtain 4.5 g of colorless liquid, i.e., compound 6, yield 76.3%.

Compound 7

The compound 6 (4.5 g, 23 mmol), MeOH (50 mL) and Pd(OH)$_2$/C (200 mg) were added into a 100 mL eggplant type bottle separately, vacuumizing was performed to replace with hydrogen three times, stirred was performed at room temperature overnight until no raw materials remained by TLC inspection, Pd(OH)$_2$/C was removed by filtration, then the pH value of the reaction solution was adjusted to acidity, and the solvent was evaporated under reduced pressure to obtain 2.8 g of white solid, i.e., compound 7, yield 85.9%.

Compound 8

-continued

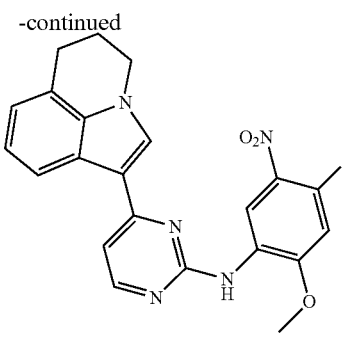

8

2,4-dichloropyrimidine (11.37 g, 76.33 mmol), aluminum trichloride (10.18 g, 76.33 mmol) and 100 mL of 1,2-dimethoxyethane (DME) were added into a 250 mL eggplant type bottle separately, and the solution was stirred at room temperature for 20 minutes. Then the compound II (10.00 g, 63.61 mmol) was added in portions, and heating was performed to 80° C. for reacting for 6 h. The reaction was stopped, the temperature was lowered to room temperature, 100 mL of water was added, the solution was stirred for 2 h, and filtered, and the solid was washed with ethanol, and dried in vacuum to obtain 15.46 g of red crude product, i.e., the compound III, yield 90.1%.

300 mL of 1,4-dioxane was added into a 500 mL eggplant type bottle, and the compound III (20.00 g, 82.07 mmol), a compound 4-fluoro-2-methoxy-5-nitroaniline (16.80 g, 90.28 mmol) and p-toluenesulfonic acid (17.17 g, 90.28 mmol) were added separately. The temperature was raised to 85° C. for reacting for 8 h, the temperature was lowered to room temperature, water was added, the solution was stirred, a 40% sodium hydroxide solution was dripped till pH=9, filtering was performed, and the solid was washed with ethanol, and dried in vacuum to obtain 30.00 g of yellow solid, i.e., compound 8, yield 92.9%.

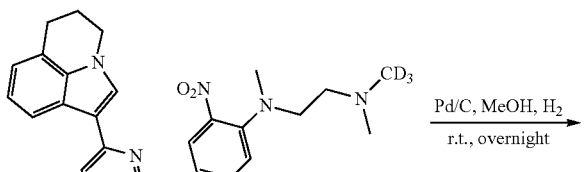

The compound 8 (2 g, 4.77 mmol), 7 (810 mg, 5.72 mmol), DIPEA (1.23 g, 9.54 mmol) and DMA (10 mL) were added into a 120 mL sealed tube. Then, the sealed tube was heated to 140° C. for reacting for 6 h, TLC was performed to ensure that no raw materials remained, the reaction solution was cooled to room temperature, 20 mL of water was added to precipitate a solid, filtering is performed, then 2 mL of methanol was added to the filter cakes, and pulping, washing, filtering, and drying were performed to obtain 1.7 g of red solid, i.e., compound 9, yield 70.6%.

Compound 10

The compound 9 (1.7 g, 3.37 mmol), Pd/C (200 mg) and MeOH (100 mL) were added into a 250 mL single-necked flask, vacuumizing was performed to replace with hydrogen for three times, stirring was performed at room temperature overnight, TLC was performed to ensure that no raw materials remained, Pd/C was removed by filtration, the solvent was evaporated under reduced pressure to obtain a yellow green solid, and the yellow green solid was purified by column chromatography, and was eluted with an eluent (DCM:MeOH:NH$_3$H$_2$O=20:1:0.1) to obtain 1.2 g of yellow green solid, i.e., compound 10, yield 75%.

Compound 11

-continued

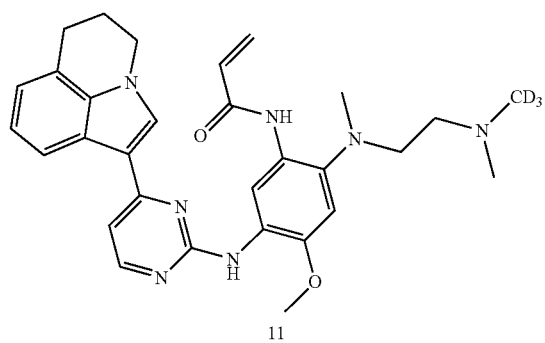

11

The compound 10 (500 mg, 1.05 mmol) and DCM (30 mL) were added into a 20 mL single-necked flask, then 3-chloropropanoyl chloride (133.7 mg, 1.05 mmol) was slowly dripped into the reaction solution at 0° C., the solution was continuously stirred at room temperature for 30 min, TLC was performed to ensure that no raw materials remained, then NaOH (168 mg, 4.2 mmol) was added, the temperature was raised to 65° C. and stirring was performed overnight, HPLC was performed to ensure that no raw materials remained, the solvent was evaporated under reduced pressure, and the product was purified by column chromatography, and eluted with an eluent (DCM:MeOH=10:1) to obtain 280 mg of light yellow solid, i.e., compound 11, yield 50.4%.

$^1$H NMR (400 MHz, CDCl3) δ 10.19 (s, 1H), 9.88 (s, 1H), 9.12 (s, 1H), 8.39 (d, J=5.3 Hz, 1H), 7.85 (d, J=8.0 Hz, 1H), 7.74 (s, 1H), 7.26-7.14 (m, 2H), 7.00 (d, J=7.0 Hz, 1H), 6.82 (s, 1H), 6.49 (dd, J=16.9, 2.2 Hz, 1H), 6.39 (dd, J=16.9, 9.8 Hz, 1H), 5.73 (dd, J=9.8, 2.2 Hz, 1H), 4.49-4.32 (m, 2H), 3.91 (s, 3H), 3.05 (t, J=6.0 Hz, 2H), 2.95-2.87 (m, 2H), 2.73 (s, 3H), 2.39-2.23 (m, 7H), 1.82 (s, 3H). LC-MS [M+H]$^+$ 528.7.

Example 2

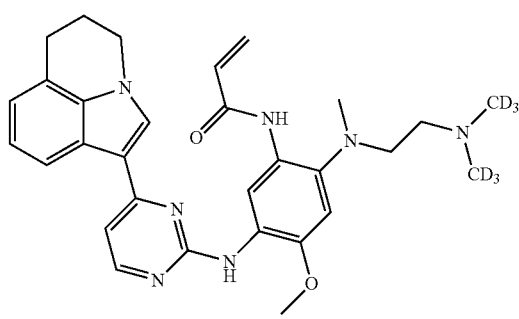 [SMILES: [2H]C([2H])([2H])N(CCN(C)c1cc(OC)c(Nc2nccc(-c3cn4c5c(cccc35)CCC4)n2)cc1NC(=O)C=C)C([2H])([2H])[2H]]

The synthetic route is as follows:

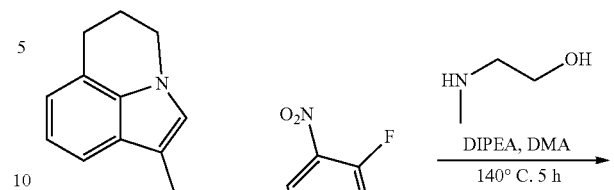

8

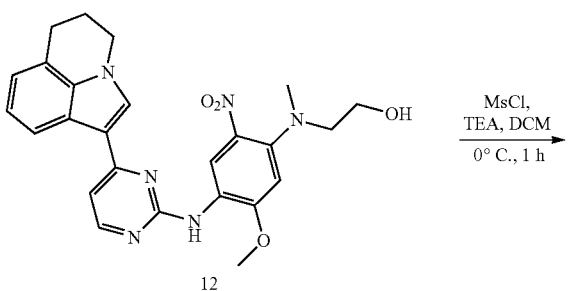

12

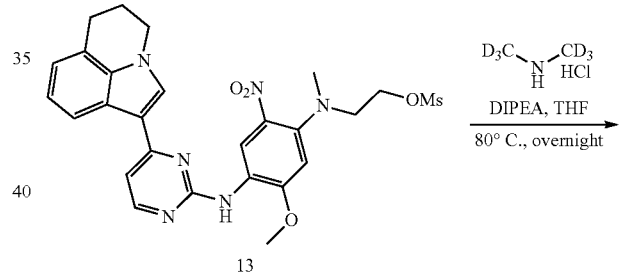

13

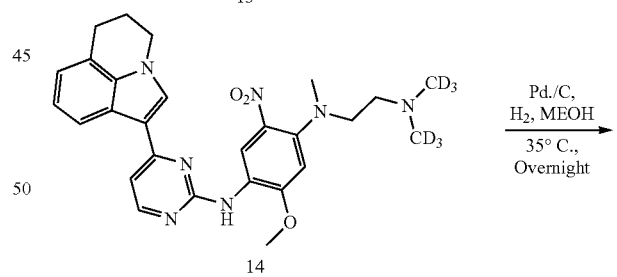

14

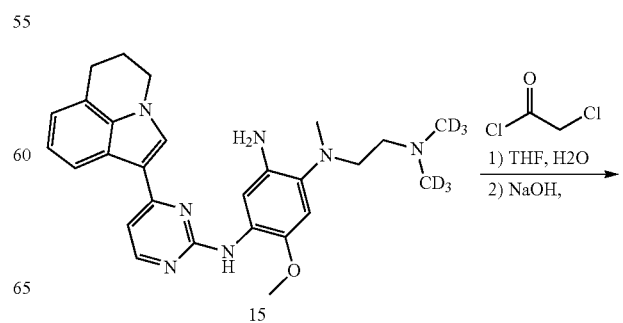

15

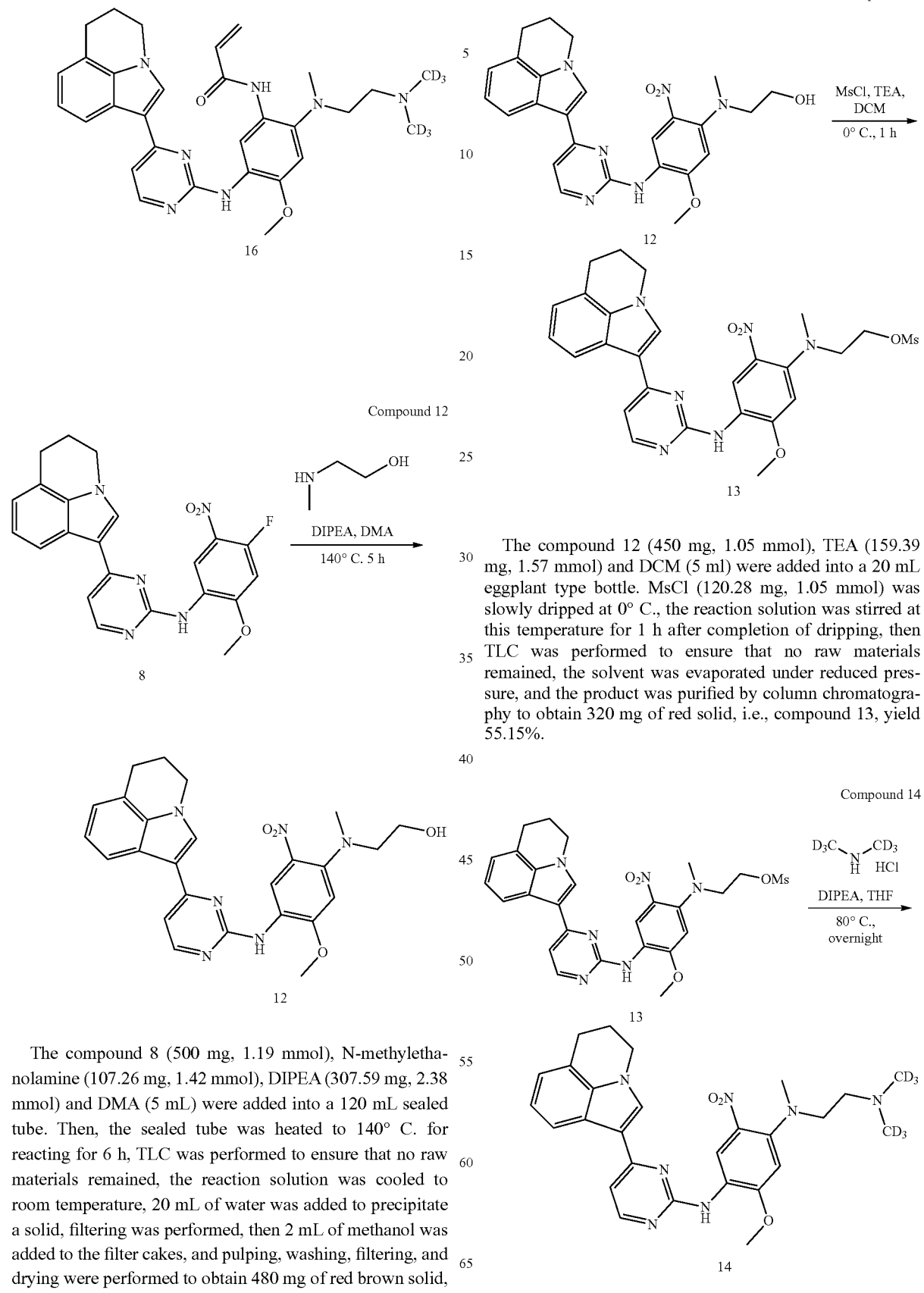

The compound 8 (500 mg, 1.19 mmol), N-methylethanolamine (107.26 mg, 1.42 mmol), DIPEA (307.59 mg, 2.38 mmol) and DMA (5 mL) were added into a 120 mL sealed tube. Then, the sealed tube was heated to 140° C. for reacting for 6 h, TLC was performed to ensure that no raw materials remained, the reaction solution was cooled to room temperature, 20 mL of water was added to precipitate a solid, filtering was performed, then 2 mL of methanol was added to the filter cakes, and pulping, washing, filtering, and drying were performed to obtain 480 mg of red brown solid, i.e., compound 12, yield 85%.

The compound 12 (450 mg, 1.05 mmol), TEA (159.39 mg, 1.57 mmol) and DCM (5 ml) were added into a 20 mL eggplant type bottle. MsCl (120.28 mg, 1.05 mmol) was slowly dripped at 0° C., the reaction solution was stirred at this temperature for 1 h after completion of dripping, then TLC was performed to ensure that no raw materials remained, the solvent was evaporated under reduced pressure, and the product was purified by column chromatography to obtain 320 mg of red solid, i.e., compound 13, yield 55.15%.

The compound 13 (220 mg, 0.40 mmol), deuterated dimethylamine (175.16 mmg, 2 mmol), DIPEA (103.39 mg, 0.8 mmol) and THF (2 mL) were added into a 5 mL sealed tube, stirring was performed at 80° C. overnight, TLC was performed to ensure that no raw materials remained, the solvent was evaporated under reduced pressure to obtain a red solid, and the red solid was purified by column chromatography, and was eluted with an eluent (DCM:MeOH:NH₃H₂O=40:1:0.1) to obtain 90 mg of red solid, i.e., compound 14, yield 44.32%.

Compound 15

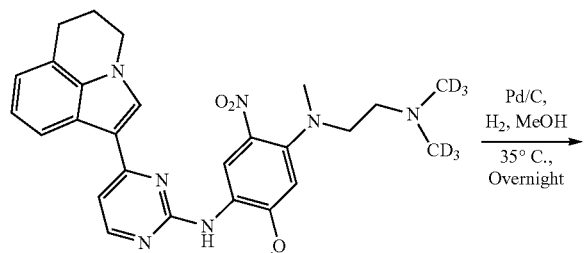

14

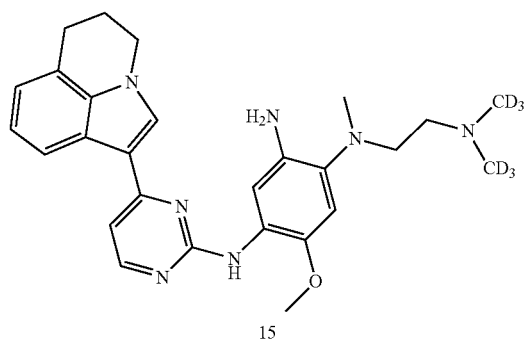

15

The compound 14 (90 mg, 0.18 mmol), Pd/C (30 mg) and MeOH (10 mL) were added into a 250 mL single-necked flask, vacuumizing was performed to replace with hydrogen for three times, stirring was performed at room temperature overnight, TLC was performed to ensure that no raw materials remained, Pd/C was removed by filtration, the solvent was evaporated under reduced pressure to obtain a yellow green solid, and the yellow green solid was purified by column chromatography, and was eluted with an eluent (DCM:MeOH:NH₃H₂O=20:1:0.1) to obtain 40 mg of yellow green solid, i.e., compound 15, yield 46.53%.

Compound 16

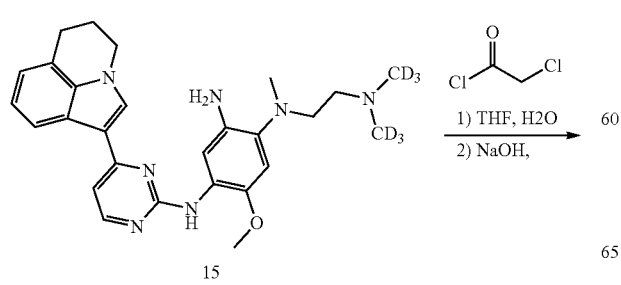

15

-continued

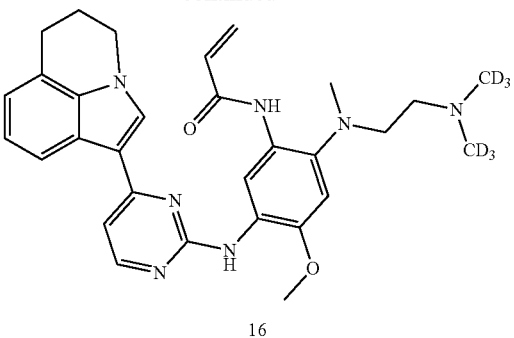

16

The compound 15 (500 mg, 0.08 mmol) and DCM (4 mL) were added into a 10 mL single-necked flask, then 3-chloropropanoyl chloride (10.63 mg, 0.08 mmol) was slowly dripped into the reaction solution at 0° C., the solution was continuously stirred at room temperature for 30 min, TLC was performed to ensure that no raw materials remained, then NaOH (16 mg, 0.4 mmol) was added, the temperature was raised to 65° C., stirring was performed overnight, TLC was performed to ensure that no raw materials remained, the solvent was evaporated under reduced pressure, purification was performed by column chromatography, and elution was performed with an eluent (DCM:MeOH:NH₃H₂O=40:1:0.1) to obtain 38 mg of light yellow solid, i.e., compound 16, yield 89.34%.

$^1$H NMR (400 MHz, CDCl3) δ 10.12 (s, 1H), 9.88 (s, 1H), 9.10 (s, 1H), 8.39 (d, J=5.2 Hz, 1H), 7.86 (d, J=8.0 Hz, 1H), 7.74 (s, 1H), 7.19 (dd, J=17.1, 6.5 Hz, 2H), 7.00 (d, J=6.9 Hz, 1H), 6.81 (s, 1H), 6.46 (d, J=8.4 Hz, 2H), 5.73 (dd, J=8.6, 3.1 Hz, 1H), 4.51-4.28 (m, 2H), 3.90 (s, 3H), 3.05 (t, J=5.6 Hz, 2H), 2.98-2.87 (m, 2H), 2.72 (s, 3H), 2.31 (dd, J=16.4, 11.2 Hz, 4H). LC-MS [M+H]⁺ 531.7.

Example 3

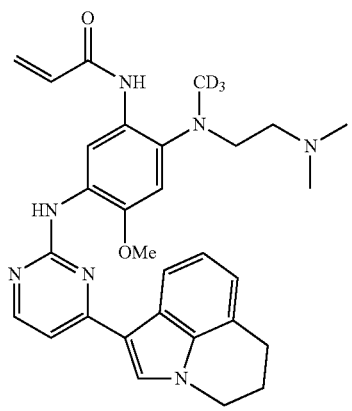 [SMILES: [2H]C([2H])([2H])N(CCN(C)C)c1cc(OC)c(Nc2nccc(-c3cn4c5c(cccc35)CCC4)n2)cc1NC(=O)C=C]

The synthetic route is as follows:

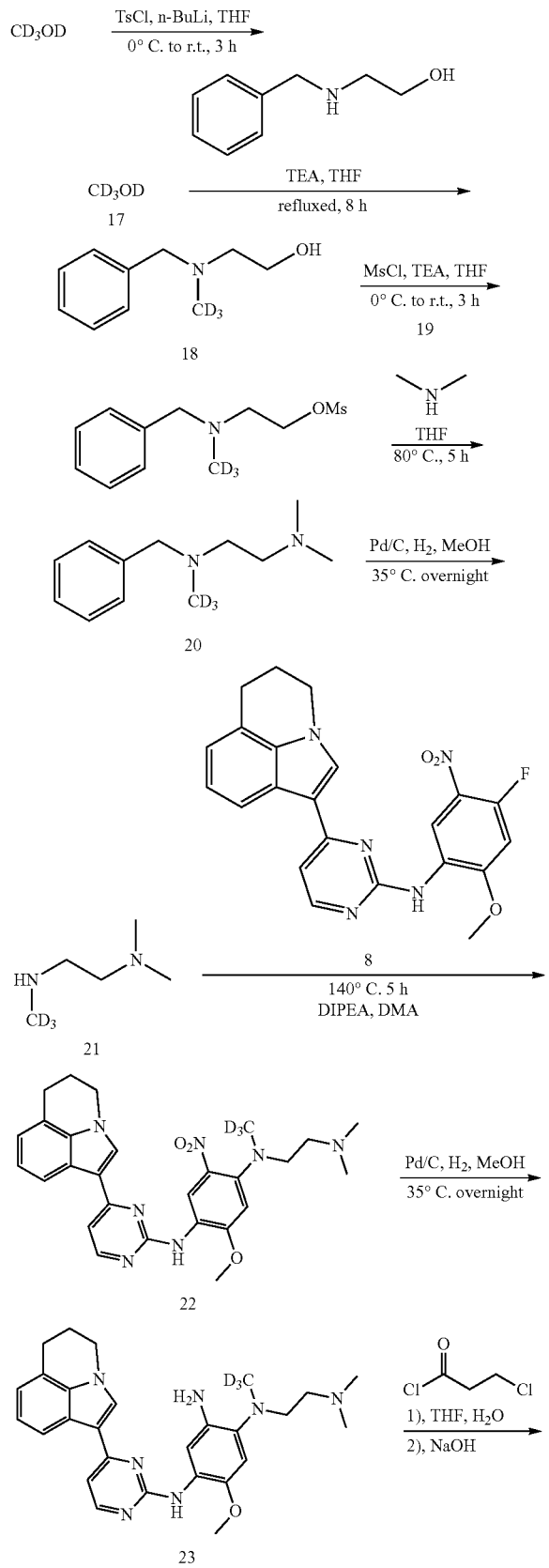

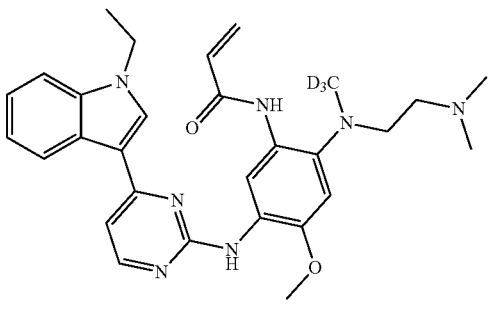

24

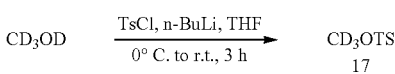

Compound 17

CD$_3$OH (15 g, 415.8 mmol) and THF (600 mL) were added into a 2 L three-necked flask separately. Then n-BuLi (174.6 mL, 436.6 mmol) was slowly dripped at −40° C. A tetrahydrofuran solution of TsCl (79.3 g, 415.8 mmol) was dripped after stirring for 1 h, then the solution was continuously stirred for 3 h, and TLC was performed to ensure that no raw materials remained. 600 mL of H$_2$O was added for quenching, extraction was performed with EA (200 mL*3), washing was performed with brine, drying over anhydrous Na$_2$SO$_4$ was performed, the organic phases were combined, the solvent was evaporated under reduced pressure to obtain a crude compound, and the crude compound was purified by column chromatography to obtain 73 g of white solid, i.e., compound 17, yield 92.7%.

Compound 18

The compound 17 (8 g, 42.3 mmol), N-benzylethanolamine (5.3 g, 35.2 mmol), triethylamine (9.8 ml, 70.4 mmol) and tetrahydrofuran (100 mL) were added into a 250 mL eggplant type bottle separately. The mixed solution was reacted for 8 h under reflux, TLC was performed to ensure that no raw materials remained, the solvent was evaporated under reduced pressure, and the product was purified by column chromatography to obtain 5 g of colorless viscous liquid, i.e., compound 18, yield 84.4%.

Compound 19

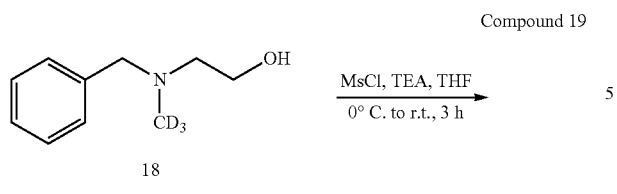

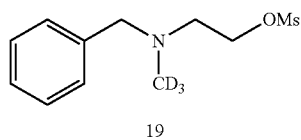

The compound 18 (3 g, 15.87 mmol), triethylamine (3.2 g, 31.74 mmol) and dichloromethane (20 mL) were added into a 50 mL eggplant type bottle separately, then mesyl chloride (2.18 g, 19.05 mmol) was slowly dripped into the reaction solution at 0° C., the reaction solution was stirred at room temperature for 3 h, TLC was performed to ensure that no raw materials remained, the solvent was evaporated under reduced pressure to obtain light yellow viscous liquid, and the liquid was purified by column chromatography to obtain 2.8 g of light yellow liquid, i.e., compound 19, yield 71.6%.

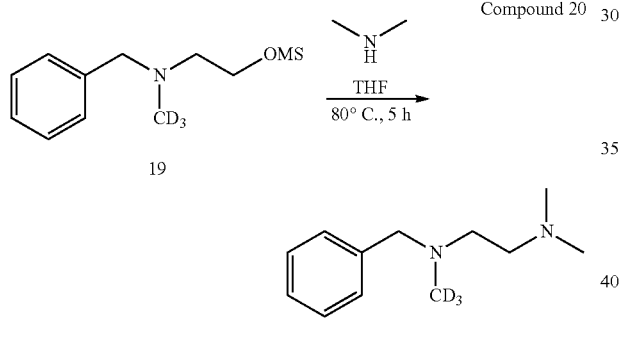

The compound 19 (2.8 g, 11.37 mmol), a dimethylamine solution (1.5 mL) and THF (3 mL) were added into a 10 mL sealed tube separately. The mixed solution was stirred at 80° C. for 5 h, and TLC was performed to ensure that no raw materials remained. 5 mL of water was added for eluting, extraction was performed with ethyl acetate (5 mL*3), the organic phases were combined, washing was performed with saturated brine, drying was performed over anhydrous $Na_2SO_4$, the solvent was evaporated under reduced pressure, and purification was performed under medium pressure to obtain 2 g of colorless liquid, i.e., compound 20, yield 75%.

Compound 21

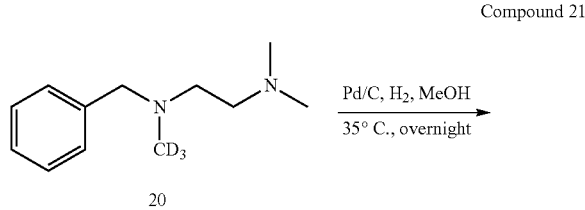

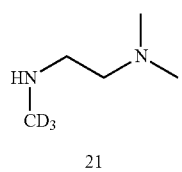

The compound 20 (2 g, 10.2 mmol), 10% palladium on carbon (500 mg) and methanol (30 mL) were added into a 100 mL eggplant type bottle separately, stirring was performed at 35° C. under hydrogen overnight, TLC was performed to ensure that no raw materials remained, the solid was filtered, HCl (in EA) was dripped to the filtrate until the pH was acidic, and the solvent was evaporated under reduced pressure to obtain 900 mg of white solid, i.e., compound 21, yield 62.3%.

Compound 22

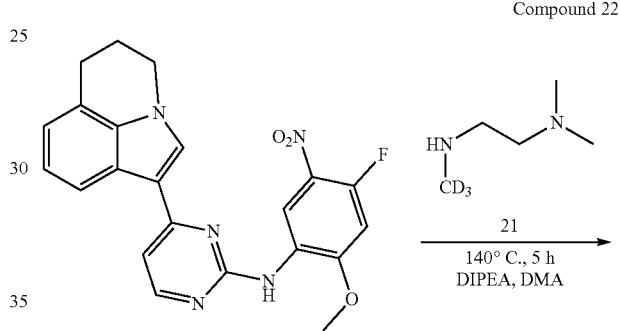

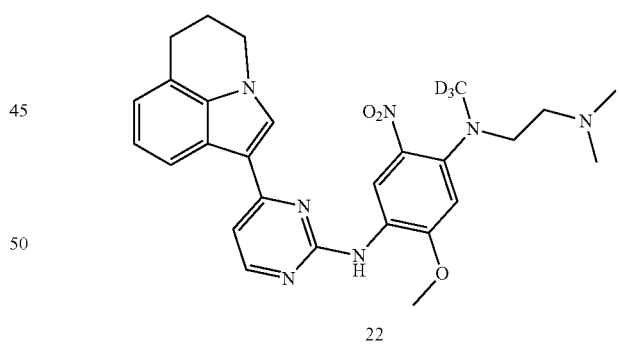

The compound 8 (965 mg, 2.3 mmol), 21 (467 mg, 2.76 mmol), diisopropylethylamine (1.18 g, 9.2 mmol) and DMA (5 mL) were added into a 120 mL sealed tube. Then, the sealed tube was heated to 140° C. for reacting for 6 h, TLC was performed to ensure that no raw materials remained, the reaction solution was cooled to room temperature, 20 mL of water was added to precipitate a solid, filtering was performed, then 2 mL of methanol was added to the filter cakes, and pulping, washing, filtering, and drying were performed to obtain 900 mg of red solid, i.e., compound 22, yield 77.5%.

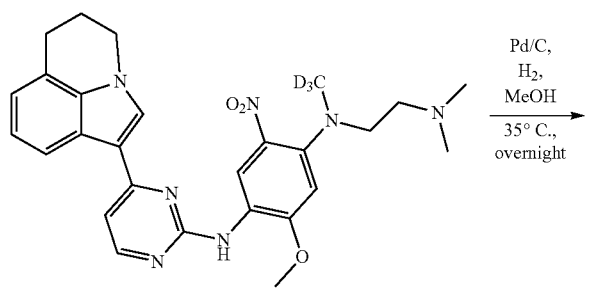

Compound 23

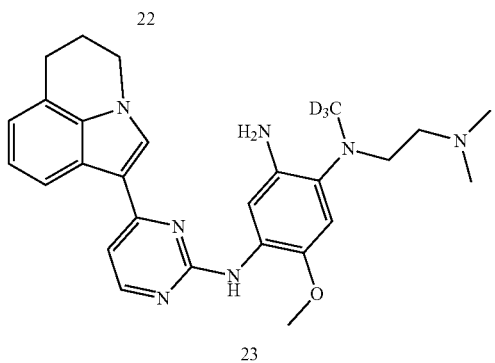

The compound 22 (900 mg, 1.78 mmol), Pd/C (300 mg) and MeOH (100 mL) were added into a 250 mL single-necked flask, vacuumizing was performed to replace with hydrogen for three times, stirring was performed at room temperature overnight, TLC was performed to ensure that no raw materials remained, Pd/C was removed by filtration, the solvent was evaporated under reduced pressure to obtain a yellow green solid, and the solid was purified by column chromatography, and was eluted with an eluent (DCM:MeOH:NH$_3$H$_2$O=20:1:0.1) to obtain 600 mg of yellow green solid, i.e., compound 23, yield 71%.

Compound 24

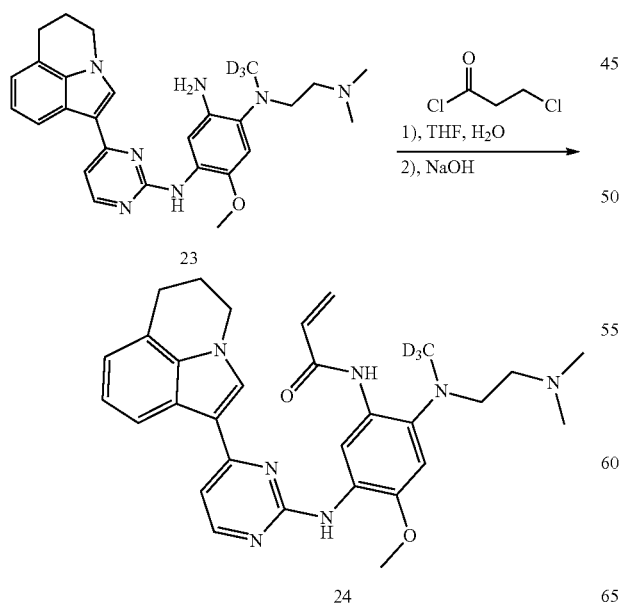

The compound 23 (300 mg, 0.63 mmol), THF (6 mL) and H$_2$O (1 mL) were added into a 20 mL single-necked flask, then 3-chloropropanoyl chloride (80.36 mg, 0.63 mmol) was slowly dripped into the reaction solution at 0° C., the solution was continuously stirred at room temperature for 30 min, TLC was performed to ensure that no raw materials remained, then NaOH (100.8 mg, 2.52 mmol) was added, the temperature was raised to 65° C., stirring was performed overnight, TLC was performed to ensure that no raw materials remained, the solvent was evaporated under reduced pressure, purification was performed by column chromatography, and elution was performed with an eluent (DCM:MeOH=10:1) to obtain 170 mg of light yellow solid, i.e., compound 24, yield 51%.

$^1$H NMR (400 MHz, CDCl3) δ 10.07 (s, 1H), 9.87 (s, 1H), 9.10 (s, 1H), 8.39 (d, J=5.3 Hz, 1H), 7.85 (d, J=8.0 Hz, 1H), 7.75 (s, 1H), 7.25-7.14 (m, 2H), 7.00 (d, J=7.0 Hz, 1H), 6.80 (s, 1H), 6.57-6.38 (m, 2H), 5.74 (dd, J=8.2, 3.8 Hz, 1H), 4.49-4.30 (m, 2H), 3.91 (s, 3H), 3.05 (t, J=6.0 Hz, 2H), 2.98-2.89 (m, 2H), 2.42-2.21 (m, 13H). LC-MS [1\4+H]$^+$ 528.7.

Example 4

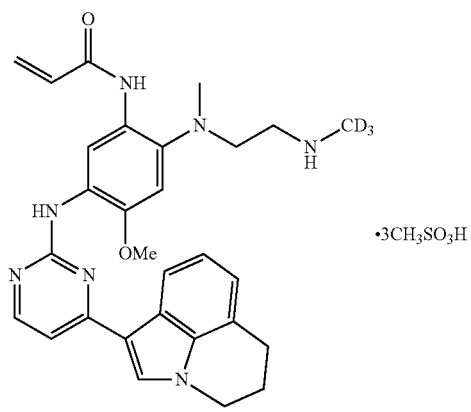 [SMILES: [2H]C([2H])([2H])NCCN(C)c1cc(OC)c(Nc2nccc(-c3cn4c5c(cccc35)CCC4)n2)cc1NC(=O)C=C]

The synthetic route is as follows:

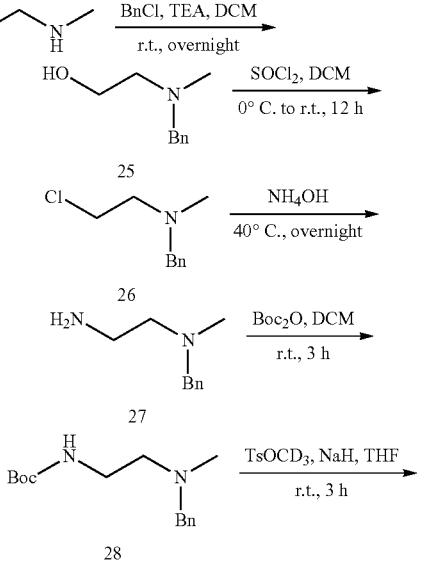

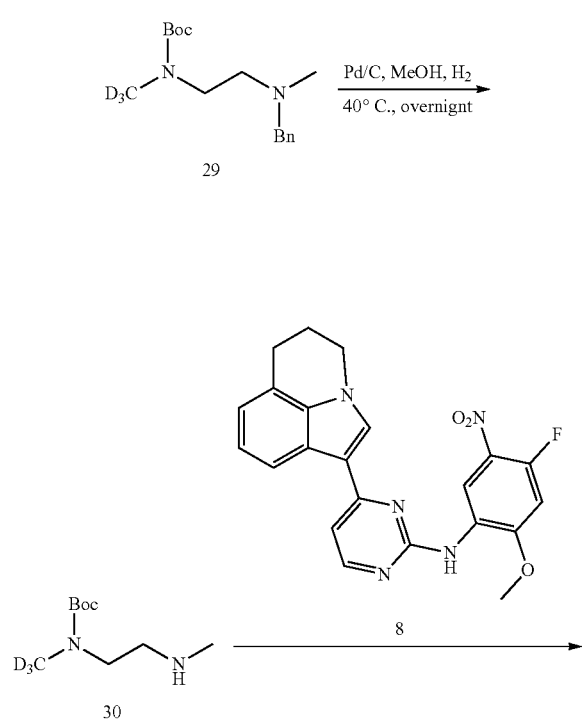

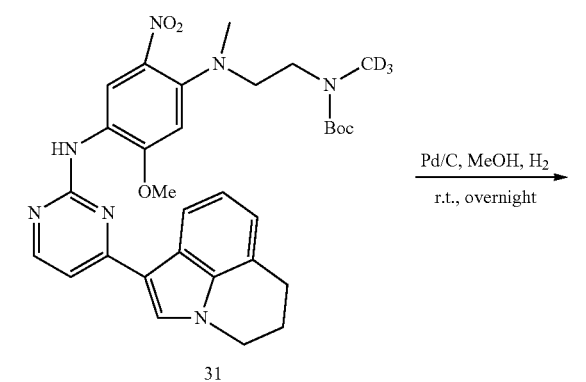

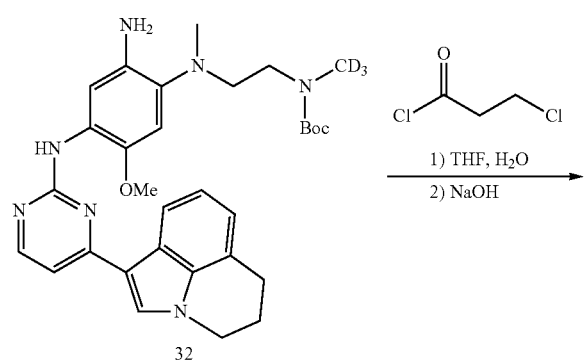

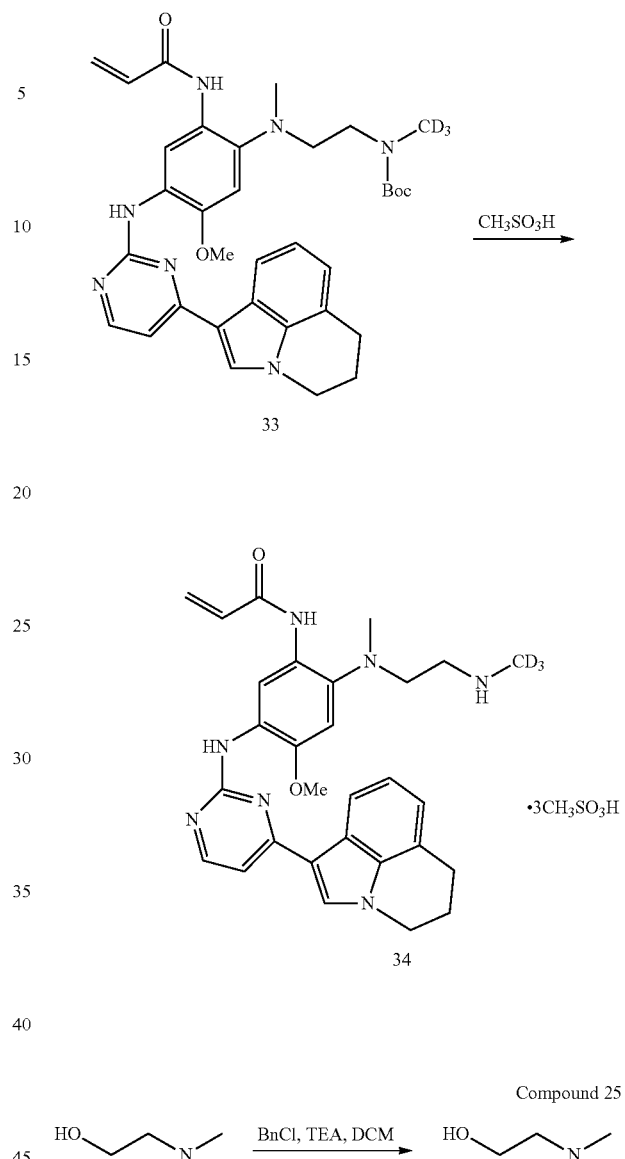

N-methylethanolamine (40.0 g, 0.532 mol), triethylamine (80.8 g, 0.8 mol) and dichloromethane (500 mL) were added into a 1 L single-necked flask separately, then benzyl chloride (67.4 g, 0.5 mol) was slowly dripped into the reaction solution at 0° C., the solution was stirred at room temperature overnight, TLC was performed to ensure that no raw materials remained, 200 mL of water was added for extracting, and an aqueous phase was extracted with 100 mL of dichloromethane. The organic phase was washed for three times with saturated brine, drying was performed over anhydrous sodium sulfate, concentration was performed under reduced pressure, and purification was performed by column chromatography to obtain 73 g of colorless liquid, i.e., product 25, yield 83.1%.

Compound 26

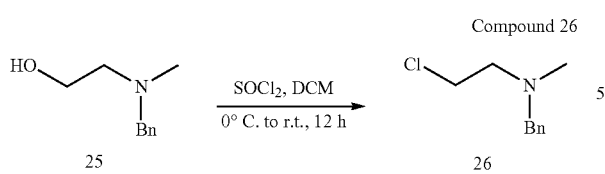

25 (71.0 g, 0.4 mol) and dichloromethane (400 mL) were added into a 1 L single-necked flask separately, thionyl chloride (76.7 g, 0.6 mol) was slowly dripped in a water bath, reaction was performed at room temperature for 12 h, and TLC was performed to ensure that no raw materials remained. Concentration was performed under reduced pressure, and purification was performed by column chromatography to obtain 60.0 g of light yellow liquid, i.e., product 26, yield 76.1%.

Compound 27

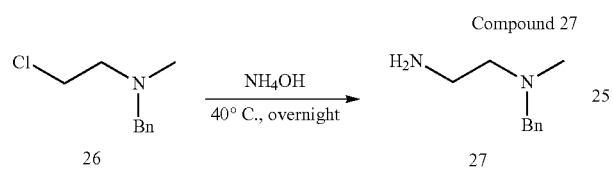

26 (60.0 g, 0.3 mol) and ammonia water (1 L) were added into a 2 L single-necked flask separately, the mixed solution was stirred at 40° C. overnight, and TLC was performed to ensure that no raw materials remained Concentration was performed under reduced pressure, and purification was performed by column chromatography to obtain a product 27 that was 40.0 g of colorless liquid, yield 74.7%.

Compound 28

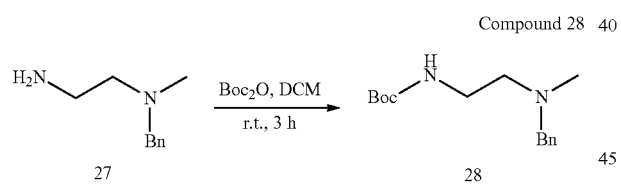

27 (40.0 g, 0.3 mol) and dichloromethane (250 mL) were added into a 1 L eggplant type bottle, Boc$_2$O (55.2 g, 0.3 mol) was slowly dripped at room temperature, then the mixed solution was continuously stirred at room temperature for 3 h, TLC was performed to ensure that no raw materials remained, the solvent was evaporated under reduced pressure, and purification was by column chromatography to obtain 58.0 g of product 28 that was colorless liquid, yield 86.7%.

Compound 29

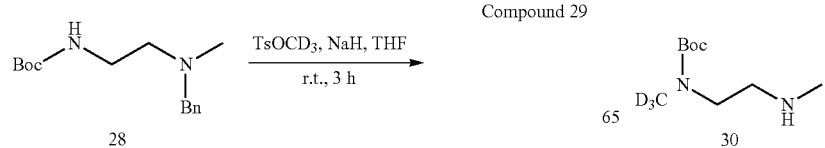

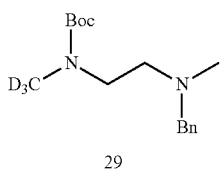

28 (26.0 g, 98.3 mmol) and N,N-dimethylformamide (100 mL) were added into a 500 mL eggplant type bottle, NaH (5.9 g, 147.5 mmol) was added in portions in an ice bath, the solution was stirred for 30 min, an N,N-dimethylformamide (10 mL) solution of TsOCD$_3$ (27.9 g, 147.5 mmol) was added, then the solution was stirred at room temperature for 3 h, TLC was performed to ensure that no raw materials remained, 300 mL of water was added for quenching, extraction was performed with ethyl acetate (100 mL*3), the organic phases were combined, washing was performed with saturated brine, drying was performed over anhydrous sodium sulfate, the solvent was evaporated under reduced pressure, and purification was performed by column chromatography to obtain 21.0 g of product 29 that was a white solid, yield 75.9%.

Compound 30

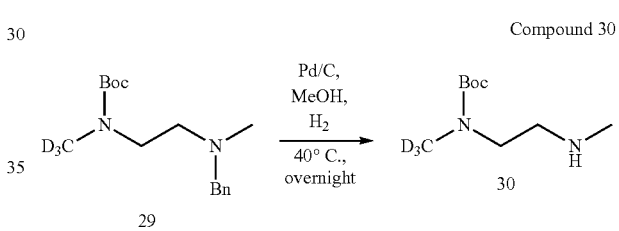

29 (21.0 g, 74.7 mmol), methanol (100 mL) and Pd/C (4.2 g) were added into a 250 mL eggplant type bottle, vacuumizing was performed to replace with hydrogen for three times, reaction was performed at 40° C. overnight, TLC was performed to ensure that no raw materials remained, Pd/C was removed by filtration, and the solvent was evaporated under reduced pressure to obtain 12.0 g of white solid, i.e., product 30, yield 84.0%.

Compound 31

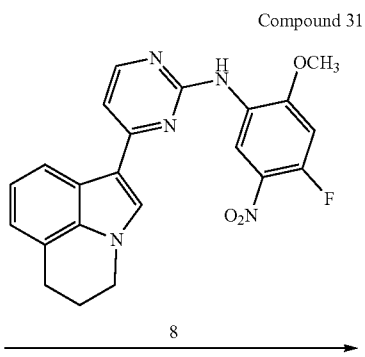

-continued

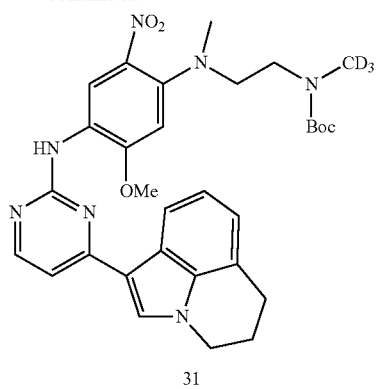

31

8 (6.1 g, 14.5 mmol), 30 (5 g, 26.1 mmol), DIPEA (3.8 g, 29 mmol) and DMAc (30 mL) were added into a 120 mL sealed tube. Then, the sealed tube was heated to 140° C. for reacting for 6 h, TLC was performed to ensure that no raw materials remained, the reaction solution was cooled to room temperature, 60 mL of water was added to precipitate a solid, filtering was performed, then 20 mL of methanol was added to the filter cakes, and pulping, washing, filtering, and drying were performed to obtain 7.0 g of red solid, i.e., product 31, yield 81.7%.

Compound 32

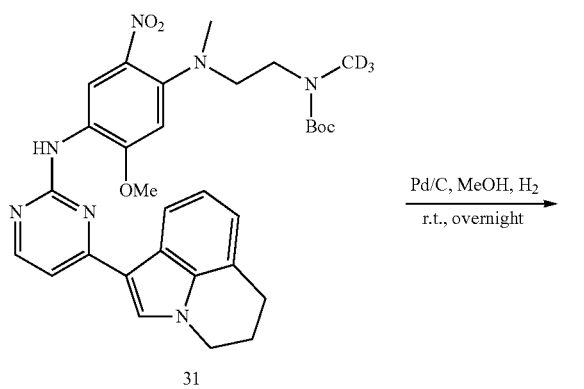

31

Pd/C, MeOH, $H_2$
r.t., overnight

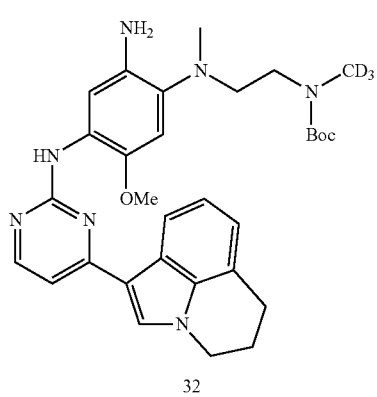

32

31 (7.0 g, 12.5 mmol), Pd/C (1.4 g) and methanol (100 mL) were added into a 250 mL single-necked flask, vacuumizing was performed to replace with hydrogen for three times, stirring was performed at room temperature overnight, TLC was performed to ensure that no raw materials remained, Pd/C was removed by filtration, the solvent was evaporated under reduced pressure to obtain a yellow green solid, and the solid was purified by column chromatography, and was eluted with an eluent (dichloromethane:methanol: ammonia water=20:1:0.1) to obtain 3.5 g of yellow green solid, i.e., product 32, yield 50.9%.

Compound 33

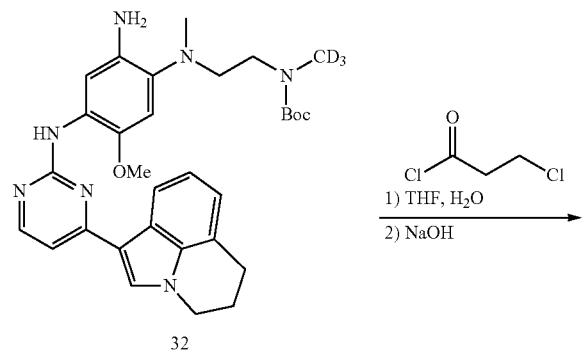

1) THF, $H_2O$
2) NaOH

33

32 (1.1 g, 2.0 mmol), tetrahydrofuran (30 mL) and water (3 mL) were added into a 100 mL single-necked flask, then 3-chloropropanoyl chloride (274 mg, 2.2 mmol) was slowly dripped into the reaction solution at 0° C., the solution was continuously stirred at room temperature for 1 h, TLC was performed to ensure that no raw materials remained, then NaOH (1.3 g, 31.4 mmol) was added, the solution was heated to 65° C. and stirred overnight, HPLC was performed to ensure that no raw materials remained, the solvent was evaporated under reduced pressure, purification was performed by column chromatography, and elution was performed with an eluent (dichloromethane:methanol:ammonia water=40:1:0.1) to obtain 800 mg of light yellow solid, i.e., product 33, yield 66.4%.

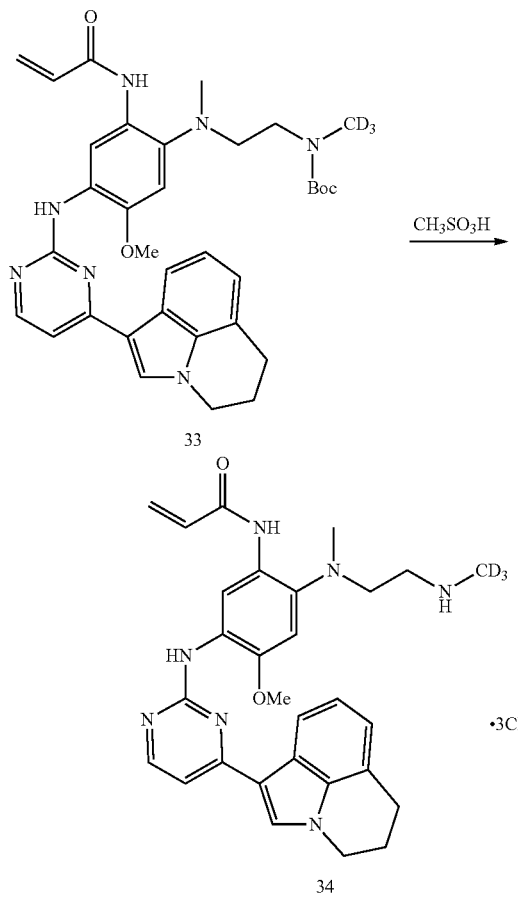

33 (320 mg, 0.5 mmol), dichloromethane (3 mL) and water (3 mL) were added into a 25 mL single-necked flask, 0.3 mL of methylsulfonic acid was slowly dripped into the reaction solution at room temperature, the solution was continuously stirred for 1 h, the dichloromethane was evaporated under reduced pressure, then 12.5 mL of ethyl acetate and 2.5 mL of ethanol were added, sonicating and crystallizing were performed during stirring at room temperature, filtering was performed, the filter cakes were washed with ethyl acetate (2 mL*2), and the filter cakes were dried to obtain 300 mg of yellow solid, i.e., product 34, yield 71.8%.

$^1$H NMR (400 MHz, DMSO) δ 9.52 (s, 1H), 8.83 (s, 1H), 8.64 (s, 2H), 8.35 (s, 1H), 8.20 (s, 1H), 7.45 (d, J=6.9 Hz, 1H), 7.06 (d, J=5.7 Hz, 3H), 6.86 (dd, J=16.9, 10.3 Hz, 1H), 6.25 (d, J=16.9 Hz, 1H), 5.77 (d, J=11.7 Hz, 1H), 4.38-4.23 (m, 2H), 3.84 (s, 3H), 3.29 (d, J=5.4 Hz, 2H), 3.21-3.18 (m, 2H), 2.97-2.92 (m, 2H), 2.66 (s, 3H), 2.19-2.11 (m, 2H), 2.41 (s, 9H).

Example 5: Biological Activity Test of Prepared Compounds

1) $IC_{50}$ test on kinase activity of these compounds against EGFR wild type, EGFR (T790M, L858R) double mutant and EGFR (L858R) single mutant. The above kinases were purchased from Invitrogen Corporation Shanghai Representative Office.

A kinase activity assay method for EGFR wild type, EGFR (T790M, L858R) double mutant and EGFR (L858R) single mutant was established by a homogeneous time-resolved fluorescence (HTRF) method to determine the inhibitory activity of the compounds. 8 μL of reaction solution was prepared, including 1×enzymatic buffer (Cisbio, HTRF KinEASE™-TK), 5 mM MgCl2, 1 mM MnCl2, 1 mM DTT, 0.5 μM TK substrate-biotin (Cisbio, HTRF KinEASE™-TK) 10 μM ATP, gradient concentration of compound and 0.04 ng/μL EGFR or 0.025 EGFR (T790M, L858R) or EGFR (L858R). The reaction concentration of the compounds was three times diluted from 1000 nM for 9 concentrations. The concentration of DMSO in the reaction system was 2%. The enzyme and the compound were pre-incubated for 15 minutes, and then ATP and substrate were added to initiate the reaction. All enzyme catalyzed reactions were carried out at 25° C. for 60 minutes. 4 μL of TK antibody-cryptate and 4 μL of streptavidin-XL665 (reaction concentration: 62.5 nM) were added when reaction was ended, and incubation was continued at 25° C. for 60 minutes. Measure the HTRF fluorescence value with CLAR-IOstar (BMG LABTECH) after the incubation, and $IC_{50}$ was determined using GraphPad Prism 5.0.

TABLE 1

| In vitro enzymatic activity test data ($IC_{50}$, nM) | | | |
|---|---|---|---|
| Compound ID | EGFR | EGFR (T790M/L858R) | EGFR (L858R) |
| AZD9291 | 20.29 | 3.328 | 5.162 |
| 11 | 38.04 | 8.066 | 11.49 |
| 16 | 27.00 | 9.116 | 11.55 |
| 24 | 15.69 | 5.017 | 8.990 |
| 34 | 35.39 | 6.843 | 14.1 |

The enzyme bioactivities of the deuterated compounds in the present invention are similar to AZD9291.

2) EGFR wild type, EGFR Exon19 deletion (activated single mutant) and EGFR (T790M, L858R) double mutant cell phosphorylation test Test 1: EGFR Wild Type Cell Phosphorylation Assay The human epidermoid carcinom cell line A431 expressed wild type EGFR and was purchased from the cell bank of the Chinese Academy of Sciences. A431 was maintained in an EMEM culture media containing 10% fetal bovine serum. The cells were grown at 37° C. in a humidified incubator containing 5% $CO_2$. Endogenous p-EGFR in the cell lysate was assayed according to Phospho-EGFR HTRF kit (Cisbio, No. #64HR1PEG). Cells were plated (50000 cells/well) in a volume of 100 μL of complete media in 96-well cell culture plates and cultured at 37° C. with 5% $CO_2$ overnight. 4-fold serial dilutions was added to the cells, the maximum concentration of the reaction being 10 μM. The cells were incubated continuously for 2 hours, 100 ng/well of EGF was added, incubated at 37° C. for 10 minutes, then the culture solution was discarded, lysis buffer (25 μL/well) was added immediately, lyse the cells at room temperature for 10 minutes, then 12 μL/well of the cell lysates were added to a Greiner white small-volume 384-well plate, detection antibodies (Anti-phospho EGFR-d2 and Anti-EGFR-Tb) were added, and the cells were incubated at 25° C. for 60 minutes. The HTRF fluorescence value was measured with CLAR-IOstar (BMG LABTECH) after the incubation, and $IC_{50}$ was determined using GraphPad Prism 5.0.

Test 2: Exon19 Deletion EGFR (Activated Single Mutant) Cell Phosphorylation Assay The human non-small cell lung cancer cell line HCC827 (Exon19 deletion EGFR, activated single mutant) was purchased from the cell bank of the Chinese Academy of Sciences. HCC827 was maintained in an RPMI1640 culture media containing 10% fetal bovine serum. The cells were grown at 37° C. in a humidified incubator containing 5% $CO_2$. Assayed the endogenous p-EGFR of the cell lysate according to the Phospho-EGFR HTRF kit (Cisbio, No. #64HR1PEG). 100 μL of cells were added to a 96-well plate (50000 cells/well), and cultured overnight at 37° C. in a cell incubator with 5% $CO_2$. 4-fold serial dilutions was added to the cells, the maximum concentration of the reaction being 10 μM. The culture solution was discarded after 2 hours' continuous incubation, lysate (25 μL/well) was added immediately, lyse the cells at room temperature for 10 minutes, then 12 μL/well of cells were added to a Greiner white small-volume 384-well plate, detection antibodies (Anti-phospho EGFR-d2 and Anti-EGFR-Tb) were added, and the cells were incubated at 25° C. for 60 minutes. The HTRF fluorescence value was measured with CLARIOstar (BMG LABTECH) after the incubation, and $IC_{50}$ was determined using GraphPad Prism 5.0.

Test 3: EGFR (T790M, L858R) Double Mutant Cell Phosphorylation Assay

The human non-small cell lung cancer cell line NCI-H1975 expressed the EGFR (T790M, L858R) double mutant and was purchased from the cell bank of the Chinese Academy of Sciences. NCI-H1975 was maintained in an RPMI1640 culture media containing 10% of fetal bovine serum. The cells were grown at 37° C. in a humidified incubator containing 5% $CO_2$. Endogenous p-EGFR in the cell lysate was assayed according to the Phospho-EGFR HTRF kit (Cisbio, No. #64HR1PEG). Cells were plated (50000 cells/well) in a volume of 100 μL of complete media in 96-well cell culture plates and cultured at 37° C. with 5% $CO_2$ overnight. 4-fold serial dilutions was added to the cells, the maximum concentration of the reaction being 10 μM. The culture solution was discarded after 2 hours' continuously incubation, lysate (25 μL/well) was added immediately, lyse the cells at room temperature for 10 minutes, then 12 μL/well of cells were added to a Greiner white small-volume 384-well plate, detection antibodies (Anti-phospho EGFR-d2 and Anti-EGFR-Tb) were added, and the cells were determined at 25° C. for 60 minutes. An HTRF fluorescence value was measured with CLARIOstar (BMG LABTECH) after the incubation, and $IC_{50}$ was calculated using GraphPad Prism 5.0.

TABLE 2

Cell level EGFR wild and mutant phosphorylation test ($IC_{50}$, nM)

| Compound ID | A431 (EGFR $^{Wild-Type}$) | NCI-H1975 (EGFR $^{T790M/L858R}$) | HCC827 (EGFR $^{del19}$) |
|---|---|---|---|
| AZD9291 | 697.8 | 53.66 | 53.85 |
| 11 | 730.1 | 85.84 | 101.1 |
| 16 | 732.3 | 94.91 | 102.8 |
| 24 | 519.9 | 85.07 | 78.07 |

The cell level bioactivities of deuterated compounds in the present invention are similar to AZD9291.

3) Assay on the Effects of the Compounds on hERG Potassium Channels

HEK293 cells stably expressing an hERG channel were cultured in 35 mm culture dishes and placed in a 37° C./5% $CO_2$ incubator for at least 24 hours before the experiment. The cell culture medium was DMEM containing 10% fetal bovine serum and 250 μg/mL G418.

The ingredients of the extracellular fluid used in the whole cell patch clamp experiment were (mM): NaCl, 137; KCl, 4; $CaCl_2$, 1.8; $MgCl_2$, 1; HEPES, 10; glucose 10; pH 7.4 (NaOH titration). All tested compounds and control compound solutions contained 0.3% DMSO. The intracellular fluid (mM) was: K Aspartate, 130; $MgCl_2$, 5; EGTA 5; HEPES, 10; Tris-ATP 4; pH 7.2 (KOH titration).

One dish was taken out for each experiment, washed twice with the extracellular fluid, and placed on an inverted microscope stage. The whole cell patch clamp experiment was performed at room temperature with a tip resistance of 3 to 5 MΩ for a borosilicate glass microelectrode. After the whole cell recording mode, the membrane potential was clamped at −80 mV, gave a +50 mV depolarization voltage stimulation to the cells every 30 s and then repolarized to −50 mV for 3 s after 2 s to elicit hERG tail current. The cells were given a −50 mV repolarization voltage for 50 ms before the depolarization voltage stimulation, and the current recorded under this voltage was used as a baseline for calculating the hERG tail current. The hERG tail current was stably recorded for at least 3 minutes in the extracellular fluid before the addition of the compound. When the amplitude change of the hERG tail current was less than 5% after perfusion administration, it was considered that the drug action reached a steady state. Data was acquired and analyzed by a pCLAMP 10.1 software program. 4 to 5 sweeps having steady current before the addition of the compound were selected to calculate a mean peak as a control current amplitude. 4 to 5 sweeps having steady current after the addition of the compound were selected to calculate a mean peak as a remaining amplitude after the current was inhibited. The inhibition rate of the tested compound to the hERG current was calculated according to the following equation:

% inhibition rate={1−(remaining current amplitude)/(control current amplitude)}×100

After the inhibition rates (mean±standard deviation) of multiple concentrations of the tested compound to the hERG current were obtained according to the above calculation method, the data was fitted using a logistic equation to obtain an IC50 value.

TABLE 3

$IC_{50}$ (μM) of inhibition of compounds on hERG potassium channels at cell level

| Compound ID | $IC_{50}$ |
|---|---|
| AZD9291 | 0.37 |
| 11 | 1.85 |
| 16 | 2.67 |
| 24 | 1.97 |

The cardiotoxicity of deuterated compounds in the present invention is lower than that of AZD9291.

What is claimed is:

1. A compound of Formula (I) or a pharmaceutically acceptable salt thereof,

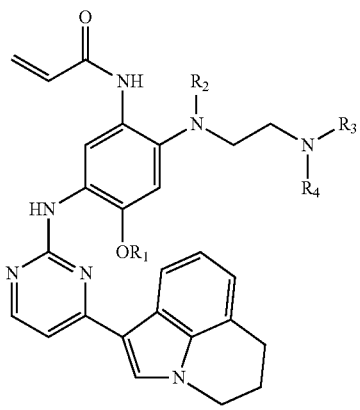

(I)

wherein: $R_1$, $R_2$, $R_3$ and $R_4$ are selected from the group consisting of —$CH_3$ and –$CD_3$, and at least one of $R_1$, $R_2$, $R_3$ and $R_4$ is —$CD_3$.

2. The compound or the pharmaceutically acceptable salt thereof according to claim 1, wherein $R_1$ is —$CH_3$.

3. The compound or the pharmaceutically acceptable salt thereof according to claim 1, wherein the compound is selected from:

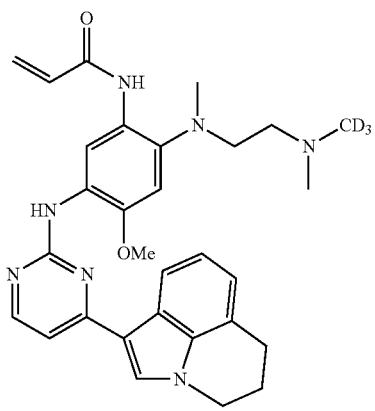

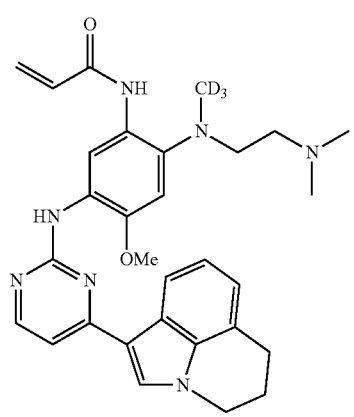

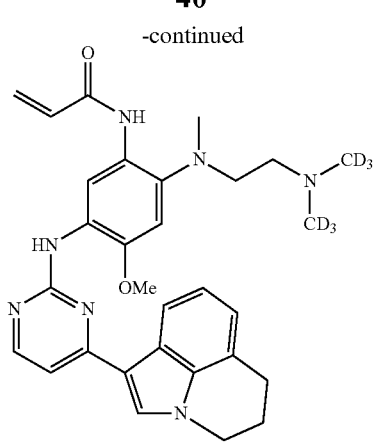

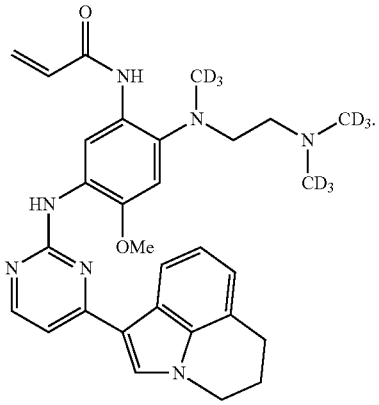

4. The compound or a pharmaceutically acceptable salt according to claim 1, wherein the pharmaceutically acceptable salt is selected from acetate, adipate, alginate, ascorbate, aspartate, benzoate, besylate, p-toluenesulfonate, hydrosulfate, borate, butyrate, citrate, camphor salt, camphor sulfonate, cyclopentane propionate, diglycolate, lauryl sulfate, ethane sulfonate, fumarate, gluceptate, glycerol phosphate, enanthate, hexanoate, hydrochloride, hydrobromide, hydroiodide, hydroxyethanesulfonate, lactate, maleate, methanesulfonate, naphthalene sulfonate, nicotinate, nitrate, oxalate, pectate, persulfate, phenpropionate, phosphate, picrate, pivalate, propionate, salicylate, succinate, sulfate, sulfonate, tartrate or thiocyanate.

5. A pharmaceutical composition, comprising an effective amount of the compound or a pharmaceutically acceptable salt thereof according to claim 1, and a pharmaceutically acceptable adjuvant.

6. A process for treating a disease comprising the step of administering to a subject in need an effective amount of the compound or a pharmaceutically acceptable salt thereof according to claim 1, wherein the disease is a tumor that is selected from non-small cell lung cancer, small cell lung cancer, pancreatic cancer, breast cancer, prostate cancer, liver cancer, skin cancer, epithelial cell cancer, gastrointestinal stromal tumor, leukemia, histiocytic lymphoma, or nasopharyngeal cancer; or the disease is associated with EGFRs or associated with EGFRs in the form of an activating mutant or a resistant mutant that is selected from non-small cell lung cancer, small cell lung cancer, pancreatic cancer, breast cancer, prostate cancer, liver cancer, skin cancer, epithelial cell cancer, gastrointestinal stromal tumor, leukemia, histiocytic lymphoma or nasopharyngeal cancer.

7. The process according to claim 6, wherein the activating mutant or a resistant mutant are selected from an L858R activating mutant, an Exon19 deletion activating mutant and a T790M resistant mutant.

* * * * *

UNITED STATES PATENT AND TRADEMARK OFFICE
CERTIFICATE OF CORRECTION

PATENT NO. : 10,654,851 B2  
APPLICATION NO. : 16/333700  
DATED : May 19, 2020  
INVENTOR(S) : Yongqiang Zhu et al.

Page 1 of 1

It is certified that error appears in the above-identified patent and that said Letters Patent is hereby corrected as shown below:

On the Title Page

(72) Inventors should read:  
Yongqiang Zhu, (Nanjing, CN); Zhaogang Liu, (Nanjing, CN); Chao Feng, (Nanjing, CN); Shihe Hu, (Nanjing, CN); Hao Chen, (Nanjing, CN); Enhe Bai, (Nanjing, CN); Jia Wang, (Nanjing, CN); Jingmiao Shi, (Nanjing, CN)

Signed and Sealed this  
Twenty-fourth Day of November, 2020

Andrei Iancu  
*Director of the United States Patent and Trademark Office*